(12) United States Patent
Lee et al.

(10) Patent No.: US 9,530,967 B2
(45) Date of Patent: *Dec. 27, 2016

(54) HETEROCYCLIC COMPOUND AND ORGANIC LIGHT-EMITTING DIODE INCLUDING THE SAME

(71) Applicant: SAMSUNG DISPLAY CO., LTD., Yongin-si, Gyeonggi-do (KR)

(72) Inventors: Jung-Sub Lee, Yongin-si (KR); Seung-Gak Yang, Yongin-si (KR)

(73) Assignee: Samsung Display Co., Ltd., Yongin-si (KR)

(*) Notice: Subject to any disclaimer, the term of this patent is extended or adjusted under 35 U.S.C. 154(b) by 919 days.

This patent is subject to a terminal disclaimer.

(21) Appl. No.: 13/633,707

(22) Filed: Oct. 2, 2012

(65) Prior Publication Data

US 2013/0200339 A1 Aug. 8, 2013

(30) Foreign Application Priority Data

Feb. 8, 2012 (KR) ........................ 10-2012-0012915

(51) Int. Cl.
*H01L 51/50* (2006.01)
*H01L 51/00* (2006.01)
*C07D 495/04* (2006.01)
*C07D 495/14* (2006.01)
*C07F 7/08* (2006.01)

(52) U.S. Cl.
CPC ......... *H01L 51/0054* (2013.01); *C07D 495/04* (2013.01); *C07D 495/14* (2013.01); *C07F 7/0812* (2013.01); *H01L 51/0067* (2013.01); *H01L 51/0071* (2013.01); *H01L 51/0072* (2013.01); *H01L 51/0081* (2013.01); *H01L 51/0085* (2013.01); *H01L 51/5016* (2013.01)

(58) Field of Classification Search
None
See application file for complete search history.

(56) References Cited

U.S. PATENT DOCUMENTS

| | | |
|---|---|---|
| 2005/0181233 A1 | 8/2005 | Sohn et al. |
| 2006/0227081 A1* | 10/2006 | Joo ..................... G09G 3/3233 345/76 |
| 2008/0124455 A1 | 5/2008 | Shin et al. |
| 2010/0013381 A1* | 1/2010 | Stoessel ................. C07C 13/62 313/504 |
| 2010/0066243 A1 | 3/2010 | Igarashi et al. |
| 2010/0230660 A1 | 9/2010 | Yokoyama et al. |
| 2011/0057175 A1 | 3/2011 | Kim et al. |
| 2011/0084259 A1* | 4/2011 | Lee .................... H01L 51/5048 257/40 |
| 2011/0156014 A1 | 6/2011 | Kim et al. |
| 2011/0297919 A1 | 12/2011 | Kwak et al. |
| 2011/0309348 A1 | 12/2011 | Kwak et al. |
| 2012/0181518 A1 | 7/2012 | Ogiwara et al. |
| 2014/0001443 A1 | 1/2014 | Lee et al. |
| 2014/0319485 A1* | 10/2014 | Lee .................... H01L 51/0067 257/40 |
| 2015/0295185 A1* | 10/2015 | Bae .................... H01L 51/0067 257/40 |

FOREIGN PATENT DOCUMENTS

| | | |
|---|---|---|
| JP | 2001-160488 | 6/2001 |
| JP | 2009-76835 | 4/2009 |
| JP | 2011-57672 A | 3/2011 |
| JP | 2011-178742 | 9/2011 |
| JP | 2011-210873 | 10/2011 |
| JP | 2011-251962 A | 12/2011 |
| JP | 2012-1538 A | 1/2012 |
| JP | 2012-156499 | 8/2012 |
| KR | 10-2005-0079727 | 8/2005 |
| KR | 10-2010-0024340 | 3/2010 |
| KR | 10-2010-0129101 | 12/2010 |
| KR | 10-2011-0068330 A | 6/2011 |
| KR | 10-2011-0137712 | 12/2011 |
| KR | 10-2012-0021215 | 3/2012 |
| KR | 10-2012-0052879 | 5/2012 |
| KR | 20120092910 A * | 8/2012 |
| KR | 10-2014-0003259 | 1/2014 |
| WO | WO 2008/020611 A1 | 2/2008 |
| WO | WO 2012/067425 A1 | 5/2012 |

OTHER PUBLICATIONS

Ueda et al., JP 2001-160488 machine translation, Date of Japanese language publication: Jun. 12, 2001, Date of machine translation: Apr. 21, 2016, pp. 1-71.*
U.S. Notice of Allowance dated Sep. 29, 2015 for cross reference U.S. Appl. No. 14/203,457, (16 pages).
SIPO Office action dated Jan. 13, 2016, with English translation, for corresponding Chinese Patent application 201210579965.1, (11 pages).
Treibs,W., Jerusalem Symposia on Quantum Chemistry and Biochemistry, (1971), STN abstract, (1 page).
STN-REGISTRY-CAS:205-57-2, Nov. 16, 1984, (3 pages).
English machine translation of Japanese Publication 2001-160488 dated Jun. 12, 2001, listed above, (12 pages).
English machine translation of Japanese Publication 2011-178742 dated Sep. 15, 2001, listed above, (33 pages).
JPO Office Action dated Sep. 6, 2016, for corresponding Japanese Patent Application No. 2013-022340 (4 pages).

* cited by examiner

*Primary Examiner* — Jennifer Chriss
*Assistant Examiner* — Dylan Kershner
(74) *Attorney, Agent, or Firm* — Lewis Roca Rothgerber Christie LLP

(57) ABSTRACT

A heterocyclic compound includes a compound represented by Formula 1.

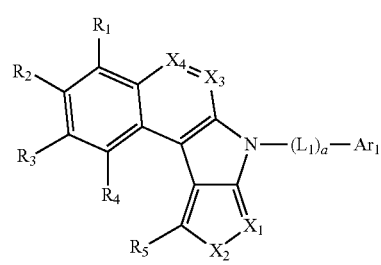

Formula 1

20 Claims, 1 Drawing Sheet

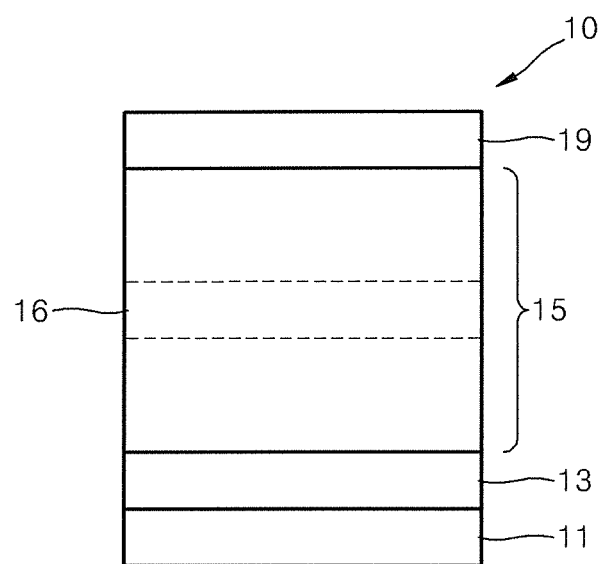

HETEROCYCLIC COMPOUND AND ORGANIC LIGHT-EMITTING DIODE INCLUDING THE SAME

CROSS-REFERENCE TO RELATED PATENT APPLICATION

This application claims priority to and the benefit of Korean Patent Application No. 10-2012-0012915, filed on Feb. 8, 2012 in the Korean Intellectual Property Office, the entire content of which is incorporated herein by reference.

BACKGROUND

1. Technical Field

The present invention relates to a heterocyclic compound and an organic light-emitting diode including the same, and more particularly, to a heterocyclic compound as an emitting material of an organic light-emitting diode, and a flat panel display device including the organic light-emitting diode.

2. Description of the Related Art

Organic light-emitting diodes (OLEDs) are self-emitting devices that have wide viewing angles, good contrast, quick response times, high brightness, and good driving voltage characteristics. Also, OLEDs can provide multicolored images. Thus, organic light-emitting diodes have drawn attention.

In general, an organic light-emitting diode has a structure including a substrate, and an anode, a hole transport layer (HTL), an emission layer (EML), an electron transport layer (ETL), and a cathode (in sequential order) stacked on the substrate. In this regard, the HTL, the EML, and the ETL are mainly formed of organic compounds. When a voltage is applied between the anode and the cathode, holes injected from the anode move to the EML via the HTL, and electrons injected from the cathode move to the EML via the ETL. Carriers, i.e., holes and electrons, recombine in the EML to generate excitons. When the excitons drop from an excited state to a ground state, light is emitted.

The emitting material is the main factor in the light emission efficiency of organic light-emitting diodes. Although fluorescent materials have widely been used as the emitting material, phosphorescent materials are known to theoretically improve light emission efficiency up to 4 times as high as general emitting materials.

4,4'-N,N'-dicarbazole-biphenyl (CBP) is widely known as a phosphorescent host material, and an organic light-emitting diode having high efficiency and good performance may be manufactured using a hole blocking material such as BCP and BAlq or using a BAlq derivative as a host.

In order to reduce the power consumption of an organic light-emitting diode, power efficiency should be improved. Since power efficiency satisfies the equation "power efficiency=($\pi$/voltage)×current efficiency," voltage should be reduced in order to improve power efficiency. Organic light-emitting diodes manufactured using phosphorescent materials have higher current efficiency than those manufactured using fluorescent materials. However, driving voltage increases when a conventional material, such as BAlq or CBP, is used as a host of the phosphorescent material instead of using a fluorescent material. Accordingly, the power efficiency cannot sufficiently be increased.

In addition, the lifespan of the organic light-emitting diodes manufactured using these host materials is not sat- isfactory. Thus, there is a need to develop a host material that is stable and has high performance.

SUMMARY OF THE INVENTION

Embodiments of the present invention provide an organic light-emitting compound with a backbone having higher emission efficiency and longer lifespan than general host materials, and having suitable color coordinates.

Embodiments of the present invention also provide an organic light-emitting diode including the organic light-emitting compound as a light-emitting material and having high efficiency and long lifespan.

Embodiments of the present invention also provide a flat panel display device including the organic light-emitting diode.

According to an embodiment of the present invention, a heterocyclic compound is represented by Formula 1 below.

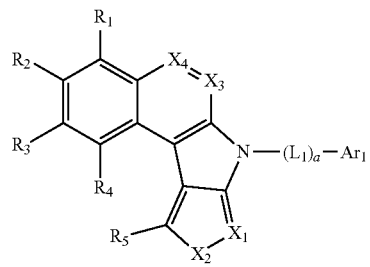

Formula 1

In Formula 1, $X_1$ is $CR_{11}$ or nitrogen (N). $X_2$ is $C(R_{12})(R_{13})$, $NR_{14}$, S, or O. $X_3$ and $X_4$ are each independently $CR_{15}$ or N. $R_1$ to $R_5$ and $R_{11}$ to $R_{15}$ are each independently a hydrogen atom, a heavy hydrogen atom, a halogen atom, a hydroxyl group, a cyano group, a nitro group, an amino group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_5$-$C_{30}$ aryl group, or a substituted or unsubstituted $C_2$-$C_{30}$ heteroaryl group. $Ar_1$ is a hydrogen atom, a heavy hydrogen atom, a halogen atom, a hydroxyl group, a cyano group, a nitro group, an amino group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_5$-$C_{30}$ aryl group, a substituted or unsubstituted $C_5$-$C_{30}$ aryloxy group, a substituted or unsubstituted $C_5$-$C_{30}$ arylthio group, a substituted or unsubstituted $C_2$-$C_{30}$ heteroaryl group, $-N(Q_1)(Q_2)$, or $-Si(Q_3)(Q_4)(Q_5)(Q_6)$. $Q_1$ to $Q_6$ are each independently a hydrogen atom, a heavy hydrogen atom, a halogen atom, a hydroxyl group, a cyano group, an amino group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_5$-$C_{30}$ aryl group, a substituted or unsubstituted $C_5$-$C_{30}$ aryloxy group, a substituted or unsubstituted $C_5$-$C_{30}$ arylthio group, or a substituted or unsubstituted $C_2$-$C_{30}$ heteroaryl group. $L_1$ is a substituted or unsubstituted $C_5$-$C_{30}$ arylene group or a substituted or unsubstituted $C_2$-$C_{30}$ heteroarylene group. Finally, a is an integer from 0 to 3.

According to another embodiment of the present invention, an organic light-emitting diode includes: a first electrode; a second electrode opposite the first electrode; and an organic layer between the first electrode and the second electrode, where the organic layer includes the heterocyclic compound represented by Formula 1.

According to another embodiment of the present invention, a flat panel display device includes a transistor that includes a source, a drain, a gate, and an active layer. The organic light-emitting diode includes the heterocyclic compound represented by Formula 1, and the first electrode of the organic light-emitting diode is electrically connected to one of the source and drain.

BRIEF DESCRIPTION OF THE DRAWINGS

The above and other features and advantages of the present invention will become more apparent by reference to the following detailed description when considered in conjunction with the attached drawing, in which:

FIG. 1 is a schematic cross-sectional view of an organic light-emitting diode according to an embodiment of the present invention.

DETAILED DESCRIPTION OF THE INVENTION

Hereinafter, exemplary embodiments of the present invention will be described in detail with reference to the accompanying drawing. As used herein, the term "and/or" includes any and all combinations of one or more of the associated listed items. Expressions such as "at least one of," when preceding a list of elements, modify the entire list of elements and do not modify the individual elements of the list.

According to an embodiment of the present invention, a heterocyclic compound is represented by Formula 1 below.

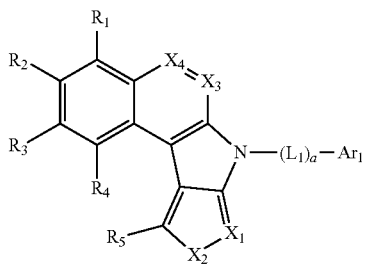

Formula 1

In Formula 1, $X_1$ is $CR_{11}$ or N. $X_2$ is $C(R_{12})(R_{13})$, $NR_{14}$, S, or O. $X_3$ and $X_4$ are each independently $CR_{15}$ or N. $R_1$ to $R_5$ and $R_{11}$ to $R_{15}$ are each independently a hydrogen atom, a heavy hydrogen atom, a halogen atom, a hydroxyl group, a cyano group, a nitro group, an amino group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_5$-$C_{30}$ aryl group, or a substituted or unsubstituted $C_2$-$C_{30}$ heteroaryl group. $Ar_1$ is a hydrogen atom, a heavy hydrogen atom, a halogen atom, a hydroxyl group, a cyano group, a nitro group, an amino group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_5$-$C_{30}$ aryl group, a substituted or unsubstituted $C_5$-$C_{30}$ aryloxy group, a substituted or unsubstituted $C_5$-$C_{30}$ arylthio group, a substituted or unsubstituted $C_2$-$C_{30}$ heteroaryl group, $-N(Q_1)(Q_2)$, or $-Si(Q_3)(Q_4)(Q_5)(Q_6)$. $L_1$ is a substituted or unsubstituted $C_5$-$C_{30}$ arylene group or a substituted or unsubstituted $C_2$-$C_{30}$ heteroarylene group. Finally, a is an integer from 0 to 3.

If there is more than one $R_{15}$, the $R_{15}$ groups may be the same or different from each other. If there is more than one $L_1$ (i.e., when a is 2 or 3), the $L_1$ groups may be the same or different. Meanwhile, if a is 0, $L_1$ is a single bond.

In the $-N(Q_1)(Q_2)$ and $-Si(Q_3)(Q_4)(Q_5)(Q_6)$, $Q_1$ to $Q_6$ are each independently a hydrogen atom, a heavy hydrogen atom, a halogen atom, a hydroxyl group, a cyano group, an amino group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_5$-$C_{30}$ aryl group, a substituted or unsubstituted $C_5$-$C_{30}$ aryloxy group, a substituted or unsubstituted $C_5$-$C_{30}$ arylthio group, or a substituted or unsubstituted $C_2$-$C_{30}$ heteroaryl group.

The heterocyclic compound represented by Formula 1 has good thermal stability due to a high glass transition temperature (Tg) and a high melting point.

The heterocyclic compound may be represented by Formula 2 when $X_4$ of Formula 1 is $CR_6$.

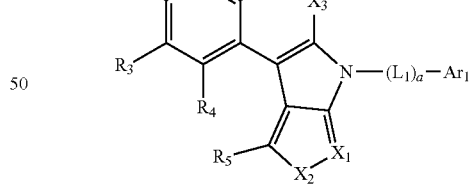

Formula 2

In Formula 2, $R_1$ to $R_6$ are each independently a hydrogen atom, a heavy hydrogen atom, a halogen atom, a hydroxyl group, a cyano group, a nitro group, an amino group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_5$-$C_{30}$ aryl group, or a substituted or unsubstituted $C_2$-$C_{30}$ heteroaryl group. $X_1$, $X_2$, $X_3$, $Ar_1$, $L_1$, and a are the same as defined above with respect to Formula 1.

The heterocyclic compound may be represented by Formula 3 when $X_1$ and $X_3$ are CH, $X_2$ is S, and $X_4$ is $CR_6$ in Formula 1.

Formula 3

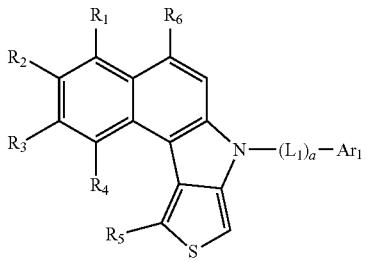

The heterocyclic compound may be represented by Formula 4 when $X_1$ is CH, $X_2$ is S, $X_3$ is N, and $X_4$ is $CR_6$ in Formula 1.

Formula 4

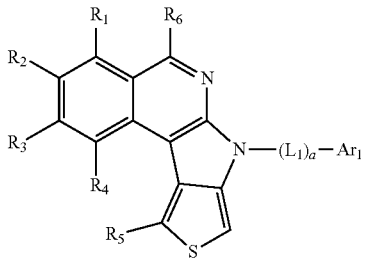

The heterocyclic compound may be represented by Formula 5 when $X_1$ is N, $X_2$ is $CH_2$, $X_3$ is N, and $X_4$ is $CR_6$ in Formula 1.

Formula 5

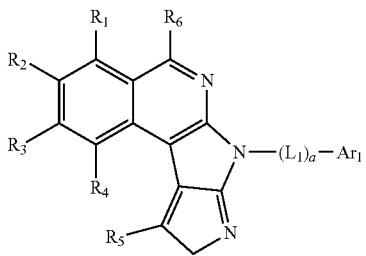

The heterocyclic compound may be represented by Formula 6 when $X_1$ is N, $X_2$ is $CH_2$, $X_3$ is N, and $X_4$ is $CR_6$ in Formula 1.

Formula 6

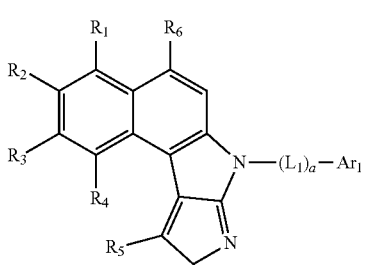

In Formulae 3 to 6, $R_1$ to $R_6$ are each independently a hydrogen atom, a heavy hydrogen atom, a halogen atom, a hydroxyl group, a cyano group, a nitro group, an amino group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_5$-$C_{30}$ aryl group, or a substituted or unsubstituted $C_2$-$C_{30}$ heteroaryl group. $Ar_1$, $L_1$, and a are the same as defined above with respect to Formula 1.

In Formula 1, $R_1$ to $R_5$ and $R_{11}$ to $R_{15}$, which are bound to the backbone of the heterocyclic compound, may each independently be a hydrogen atom, a heavy hydrogen atom, a substituted or unsubstituted $C_1$-$C_{30}$ alkyl group, a substituted or unsubstituted $C_5$-$C_{30}$ aryl group, or a substituted or unsubstituted $C_2$-$C_{30}$ heteroaryl group. For example, $R_1$ to $R_5$ and $R_{11}$ to $R_{15}$ may each independently be a hydrogen atom, a heavy hydrogen atom, a substituted or unsubstituted methyl group, a substituted or unsubstituted ethyl group, a substituted or unsubstituted propyl group, a substituted or unsubstituted butyl group, a substituted or unsubstituted phenyl group, a substituted or unsubstituted biphenyl group, a substituted or unsubstituted naphthyl group, a substituted or unsubstituted anthryl group, a substituted or unsubstituted phenanthrenyl group, a substituted or unsubstituted pyrenyl group, a substituted or unsubstituted indolyl group, a substituted or unsubstituted indenyl group, a substituted or unsubstituted fluorenyl group, or a substituted or unsubstituted carbazolyl group.

In Formula 1, $Ar_1$, which is bound to the backbone of the heterocyclic compound via the linking group $L_1$, may be a substituted or unsubstituted $C_5$-$C_{30}$ aryl group, a substituted or unsubstituted $C_5$-$C_{30}$ aryloxy group, a substituted or unsubstituted $C_5$-$C_{30}$ arylthio group, a substituted or unsubstituted $C_2$-$C_{30}$ heteroaryl group, —N($Q_1$)($Q_2$), or —Si($Q_3$)($Q_4$)($Q_5$)($Q_6$). In this regard, $Q_1$ to $Q_6$ may each independently be a hydrogen atom, a heavy hydrogen atom, a substituted or unsubstituted $C_1$-$C_{30}$ alkyl group, a substituted or unsubstituted $C_5$-$C_{30}$ aryl group, or a substituted or unsubstituted $C_2$-$C_{30}$ heteroaryl group. For example, $Ar_1$ may be a hydrogen atom, a heavy hydrogen atom, a substituted or unsubstituted $C_1$-$C_{30}$ alkyl group, a substituted or unsubstituted $C_1$-$C_{20}$ alkoxy group, a substituted or unsubstituted phenyl group, a substituted or unsubstituted pentalenyl group, a substituted or unsubstituted indenyl group, a substituted or unsubstituted naphthyl group, a substituted or unsubstituted azulenyl group, a substituted or unsubstituted heptalenyl group, a substituted or unsubstituted indacenyl, a substituted or unsubstituted acenaphthyl group, a substituted or unsubstituted fluorenyl group, a substituted or unsubstituted spiro-fluorenyl group, a substituted or unsubstituted phenalenyl group, a substituted or unsubstituted phenanthrenyl group, a substituted or unsubstituted anthryl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentaphenyl group, a substituted or unsubstituted hexacenyl group, a substituted or unsubstituted pyrrolyl group, a substituted or unsubstituted imidazolyl group, a substituted or unsubstituted pyrazolyl group, a substituted or unsubstituted pyridinyl group, a substituted or unsubstituted pyrazinyl group, a substituted or unsubstituted pyrimidinyl group, a substituted or unsubstituted pyridazinyl group, a substituted or unsubstituted isoindolyl group, a substituted or unsubstituted indolyl group, a substituted or unsubstituted indazolyl group, a substituted or unsubstituted purinyl group, a substituted or unsubstituted quinolinyl group, a substituted or unsubstituted benzoquinolinyl group, a substituted or unsubstituted phthalazinyl group, a substituted or unsubstituted naphthyridinyl group, a substituted or unsubstituted quinoxalinyl group, a substituted or unsubstituted quinazolinyl group, a substituted or unsubstituted cinnolinyl group, a substituted or unsubstituted carbazolyl group, a substituted or unsubstituted phenanthridinyl group, a substituted or unsubstituted acridinyl group, a substituted or unsubstituted phenanthrolinyl group, a substituted or unsubstituted phenazinyl group, a substituted or unsubstituted benzooxazolyl group, a substituted or unsubstituted benzoimidazolyl group, a substituted or unsubstituted furanyl group, a substituted or unsubstituted benzofuranyl group, a substituted or unsubstituted thiophenyl group, a substituted or unsubstituted benzothiophenyl group, a substituted or unsubstituted thiazolyl group, a substituted or unsubstituted isothiazolyl group, a substituted or unsubstituted benzothiazolyl group, a substituted or unsubstituted isoxazolyl group, a substituted or unsubstituted oxazolyl group, a substituted or unsubstituted triazolyl group, a substituted or unsubstituted tetrazolyl group, a substituted or unsubstituted oxadiazolyl group, a substituted or unsubstituted triazinyl group, a substituted or unsubstituted benzooxazolyl group, a substituted or unsubstituted dibenzopuranyl group, a substituted or unsubstituted dibenzothiophenyl group, a substituted or unsubstituted benzocarbazolyl group, or a substituted or unsubstituted tetraphenylsilanyl group.

In Formula 1, $Ar_1$ may be one of the compounds represented by Formulae 7-1 to 7-12 below:

7-1
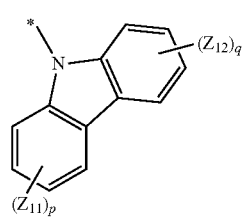

7-2
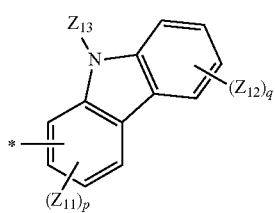

7-3
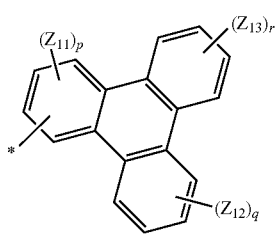

7-4
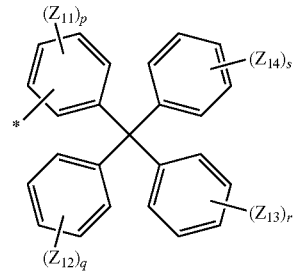

7-5
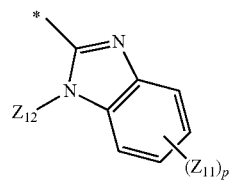

7-6
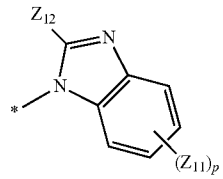

7-7
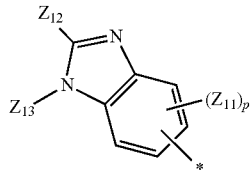

7-8
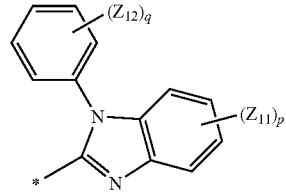

7-9
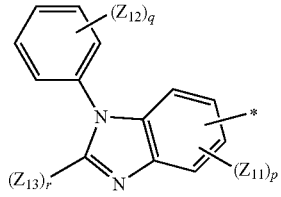

7-10
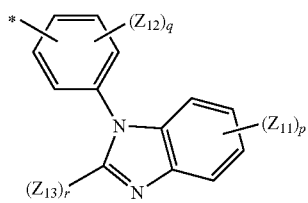

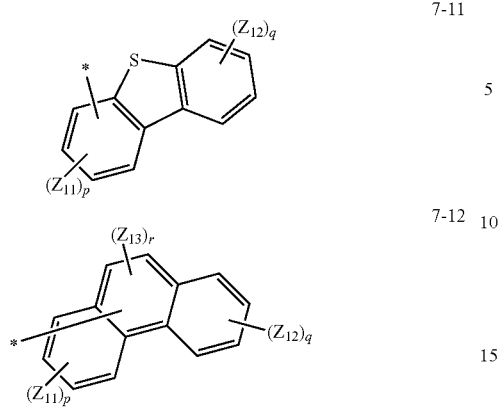

7-11

7-12

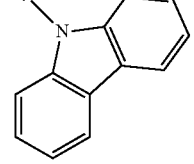
8-1

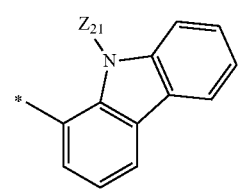
8-2

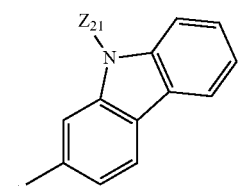
8-3

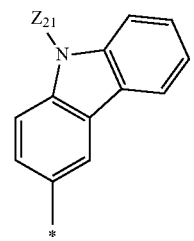
8-4

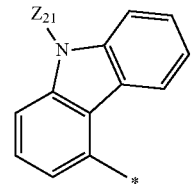
8-5

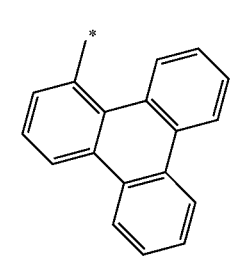
8-6

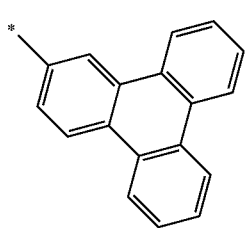
8-7

In Formulae 7-1 to 7-12, $Z_{11}$ to $Z_{14}$ are each independently a hydrogen atom; a heavy hydrogen atom; a halogen atom; a hydroxyl group; a cyano group; a nitro group; an amino group; an amidino group; hydrazine; hydrazone; a carboxyl group or a salt thereof; a sulfonic acid group or a salt thereof; a phosphoric acid group or a salt thereof; a $C_1$-$C_{10}$ alkyl group; a $C_1$-$C_{10}$ alkoxy group; a $C_1$-$C_{10}$ alkyl group or a $C_1$-$C_{10}$ alkoxy group substituted with at least one of a heavy hydrogen atom, a halogen atom, a hydroxyl group, a cyano group, a nitro group, an amino group, an amidino group, hydrazine, hydrazone, a carboxyl group or a salt thereof, a sulfonic acid group or a salt thereof, and/or a phosphoric acid group or a salt thereof; a phenyl group; a naphthyl group; a fluorenyl group; a phenanthrenyl group; an anthryl group; a pyrenyl group; a chrysenyl group; a phenyl group, a naphthyl group, a fluorenyl group, a phenanthrenyl group, an anthryl group, a pyrenyl group, or a chrysenyl group substituted with at least one of a heavy hydrogen atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{10}$ alkyl group, and/or a $C_1$-$C_{10}$ alkoxy group; an indolyl group; a benzoimidazolyl group; a carbazolyl group; an imidazolyl group; an imidazolinyl group; an imidazopyridinyl group; an imidazopyrimidinyl group; a pyridinyl group; a pyrimidinyl; a triazinyl group; a quinolinyl group; or an indolyl group, a benzoimidazolyl group, a carbazolyl group, an imidazolyl group, an imidazolinyl group, an imidazopyridinyl group, a pyridinyl group, a pyrimidinyl group, a triazinyl group, or a quinolinyl group substituted with at least one of a heavy hydrogen atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, and/or a naphthyl group. Each of p, q, r, and s is independently an integer from 1 to 5.

If there are more than one of any of $Z_{11}$ to $Z_{14}$, i.e., when p, q, r or s is greater than 1, the respective Z groups may be the same or different from each other. The "*" indicates a binding site between $Ar_1$ and the remainder of the compound of Formula 1.

For example, in Formula 1, $Ar_1$ may be one of the compounds represented by Formulae 8-1 to 8-20 below:

8-8
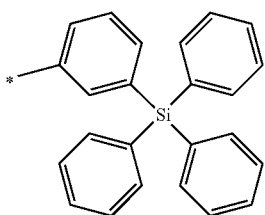

8-9
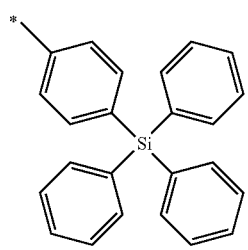

8-10
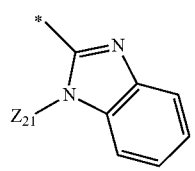

8-11
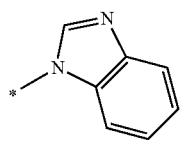

8-12
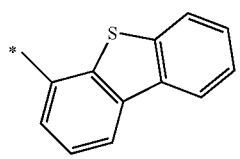

8-13
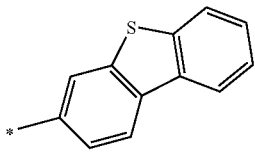

8-14
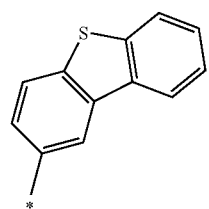

8-15
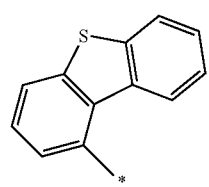

8-16
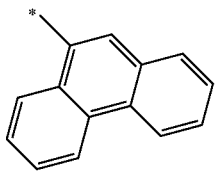

8-17
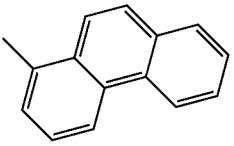

8-18
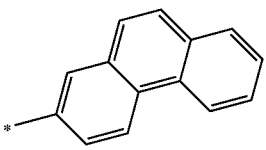

8-19
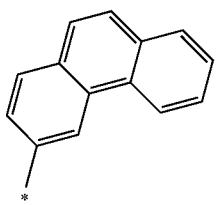

8-20
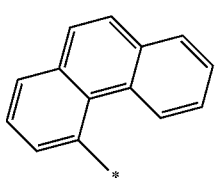

In Formulae 8-1 to 8-20, $Z_{21}$ may be a hydrogen atom, a heavy hydrogen atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a fluorenyl group, a phenanthrenyl group, an anthryl group, a pyrenyl group, a chrysenyl group, an indolyl group, a benzoimidazolyl group, a carbazolyl group, an imidazolyl group, an imidazolinyl group, an imidazopyridinyl group, an imidazopyrimidinyl group, a pyridinyl group, a pyrimidinyl group, a triazinyl group, or a quinolinyl group. The "*" indicates a binding site between $Ar_1$ and the remainder of the compound of Formula 1.

In Formula 1, the backbone of the heterocyclic compound is bound to $Ar_1$ via a linking group $L_1$. $L_1$ may be a substituted or unsubstituted phenylene group, a substituted or unsubstituted pentalenylene group, a substituted or unsubstituted indenylene group, a substituted or unsubstituted naphthylene group, a substituted or unsubstituted azulenylene group, a substituted or unsubstituted heptalenylene group, a substituted or unsubstituted indacenylene group, a substituted or unsubstituted acenaphthylene group, a substituted or unsubstituted fluorenylene group, a substituted or unsubstituted phenalenylene group, a substituted or unsubstituted phenanthrenylene group, a substituted or unsubstituted anthrylene group, a substituted or unsubstituted fluoranthenylene group, a substituted or unsubstituted triphenylenylene group, a substituted or unsubstituted pyrenylene group, a substituted or unsubstituted chrysenylene group, a substituted or unsubstituted naphthacenylene group, a substituted or unsubstituted picenylene group, a substituted or unsubstituted perylenylene group, a substituted or unsubstituted pentaphenylene group, a substituted or unsubstituted hexacenylene group, a substituted or unsubstituted pyrrolylene group, a substituted or unsubstituted pyrazolylene group, a substituted or unsubstituted imidazolylene group, a substituted or unsubstituted imidazolinylene group, a substituted or unsubstituted imidazopyridinylene group, a substituted or unsubstituted imidazopyrimidinylene group, a substituted or unsubstituted pyridinylene group, a substituted or unsubstituted pyrazinylene group, a substituted or unsubstituted pyrimidinylene group, a substituted or unsubstituted indolylene group, a substituted or unsubstituted purinylene group, a substituted or unsubstituted quinolinylene group, a substituted or unsubstituted phthalazinylene group, a substituted or unsubstituted indolizinylene group, a substituted or unsubstituted naphthyridinylene group, a substituted or unsubstituted quinazolinylene group, a substituted or unsubstituted cinnolinylene group, a substituted or unsubstituted indazolylene group, a substituted or unsubstituted carbazolylene group, a substituted or unsubstituted phenazinylene group, a substituted or unsubstituted phenanthridinylene group, a substituted or unsubstituted pyranylene group, a substituted or unsubstituted chromenylene group, a substituted or unsubstituted furanylene group, a substituted or unsubstituted benzofuranylene group, a substituted or unsubstituted thiophenylene group, a substituted or unsubstituted benzothiophenylene group, a substituted or unsubstituted isothiazolylene group, a substituted or unsubstituted benzoimidazolylene group, a substituted or unsubstituted isoxazolylene group, a substituted or unsubstituted dibenzothiophenylene group, a substituted or unsubstituted dibenzopuranylene group, a substituted or unsubstituted triazinylene group, or a substituted or unsubstituted oxadiazolylene group.

For example, in Formula 1, $L_1$ may be one of the compounds represented by Formulae 9-1 to 9-17 below:

9-1

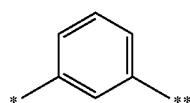

9-2

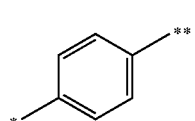

9-3

9-4

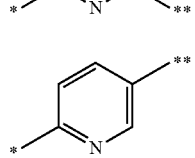

9-5

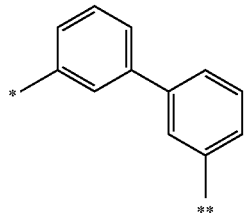

9-6

9-7

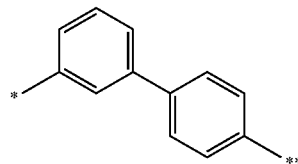

9-8

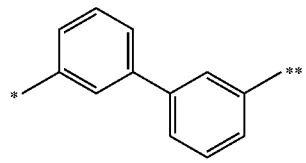

9-9

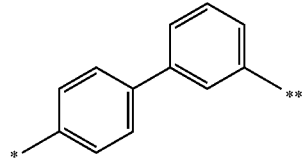

9-10

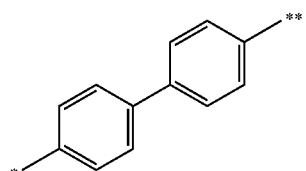

9-11

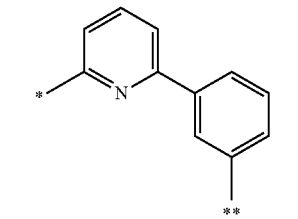

9-12

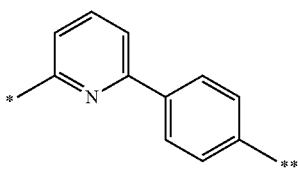

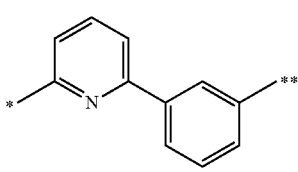

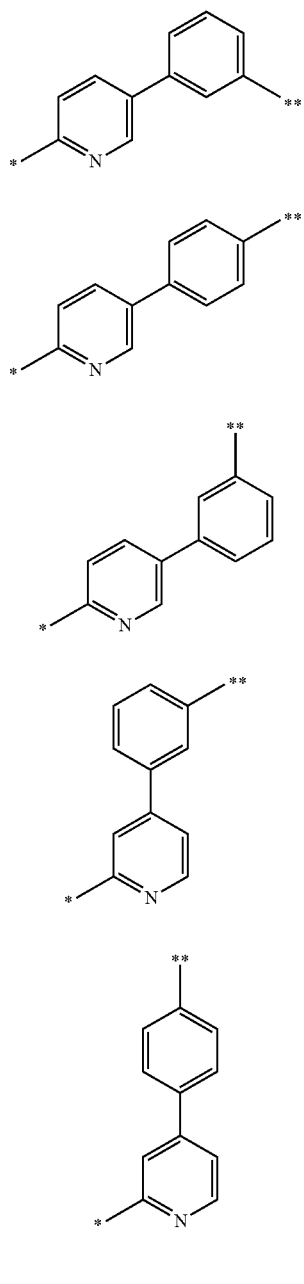
The heterocyclic compound represented by Formula 1 may be any one compound of Compounds 1 to 48 below, but is not limited thereto.
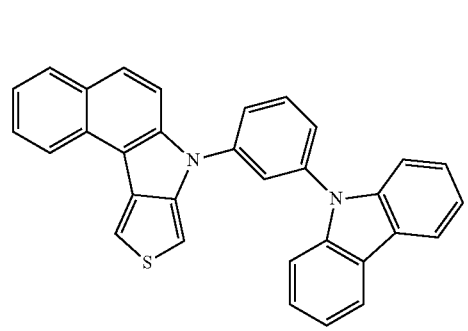
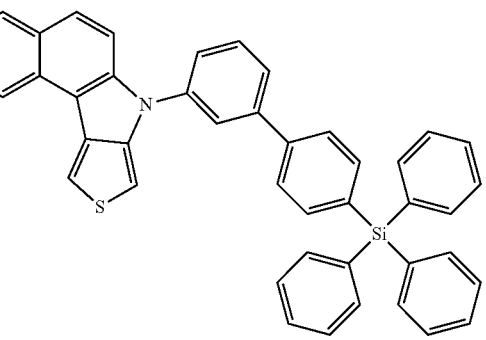

-continued

15
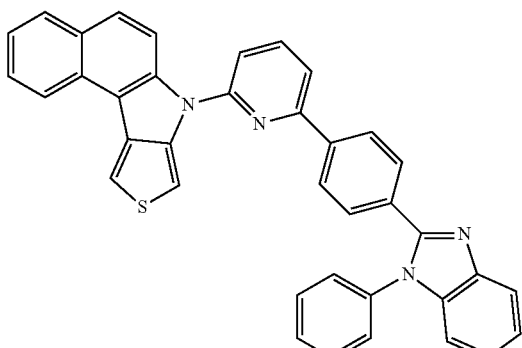
16
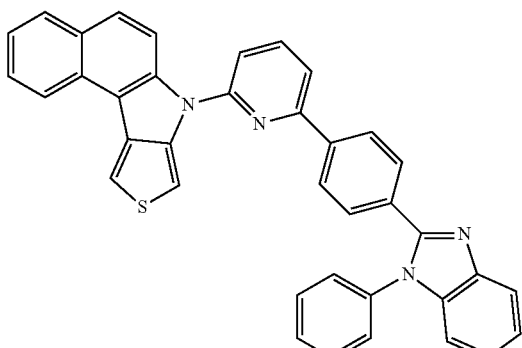
17
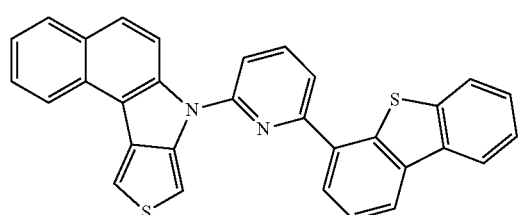
18
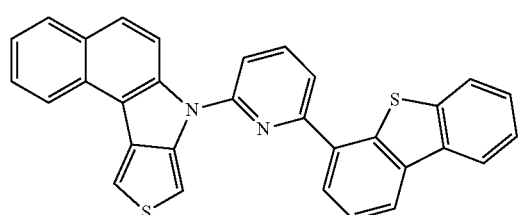
19
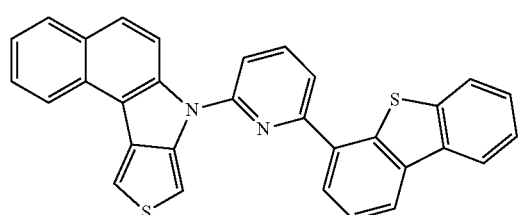
20
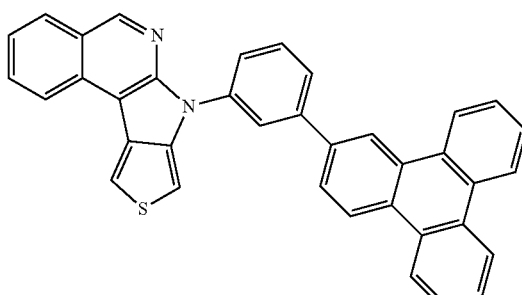
21
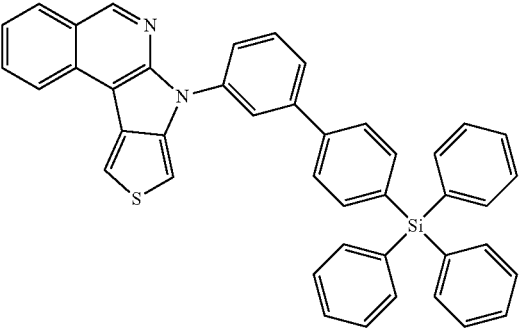
22
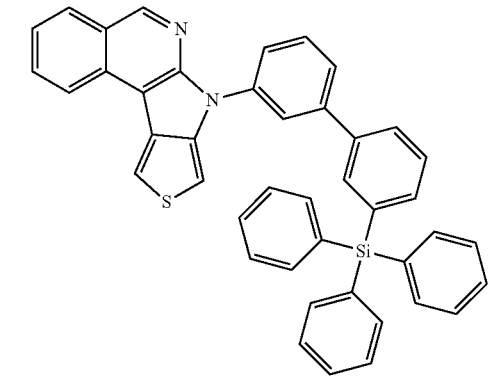
23
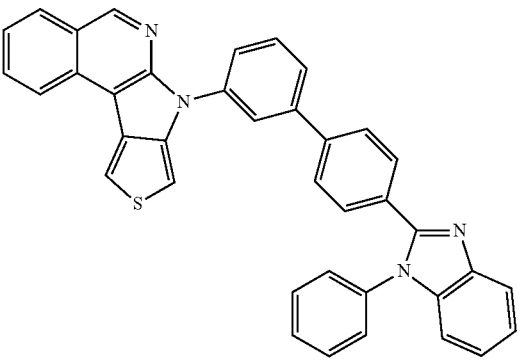

24
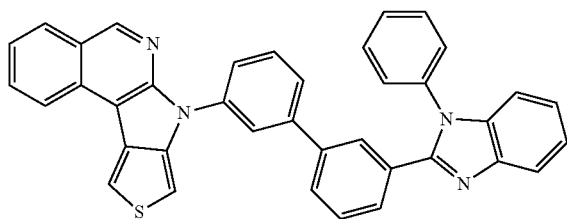
25
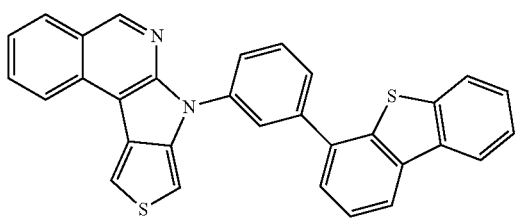
26
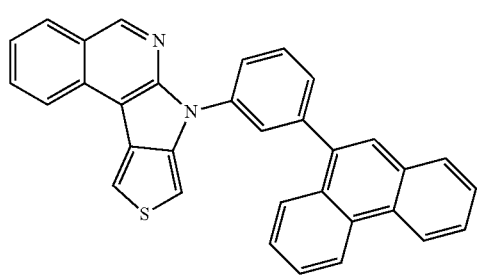
27
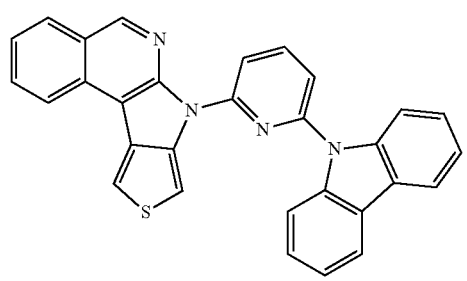
28
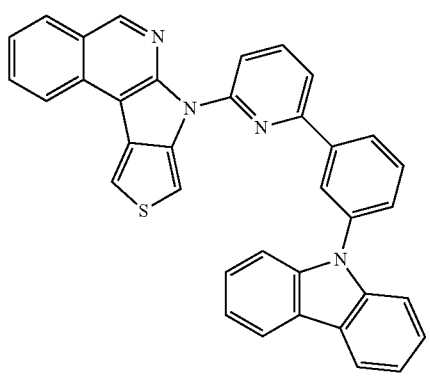
29
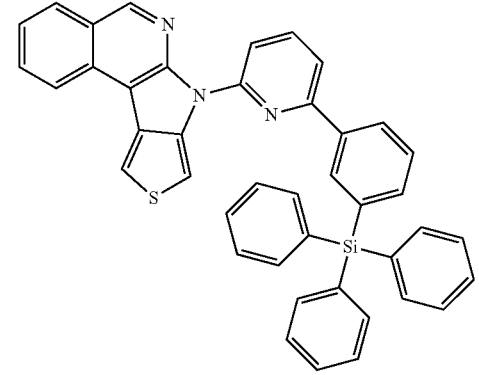
30
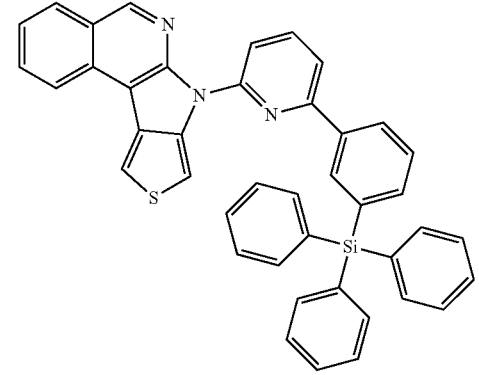
31
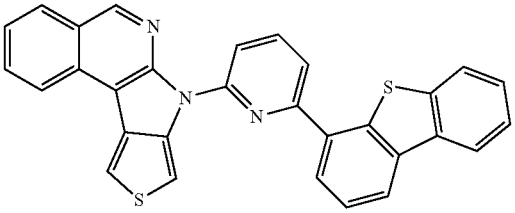
32
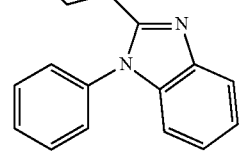
33
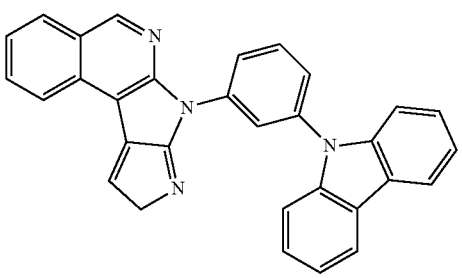

34
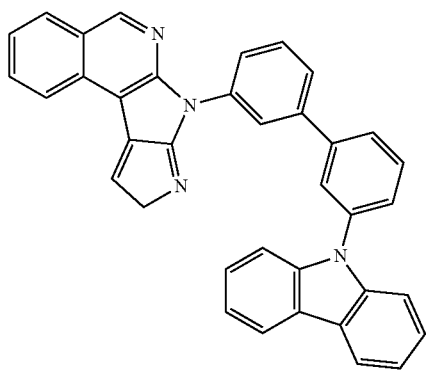
35
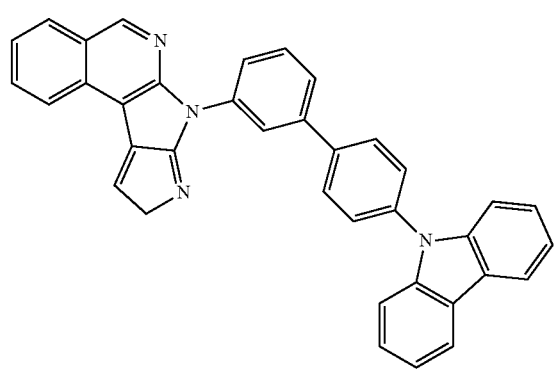
36
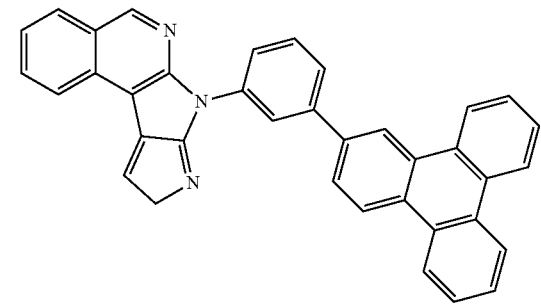
37
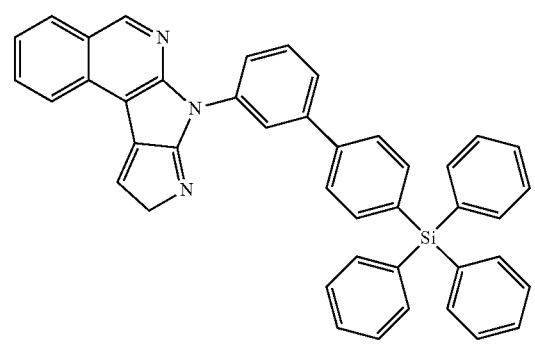
38
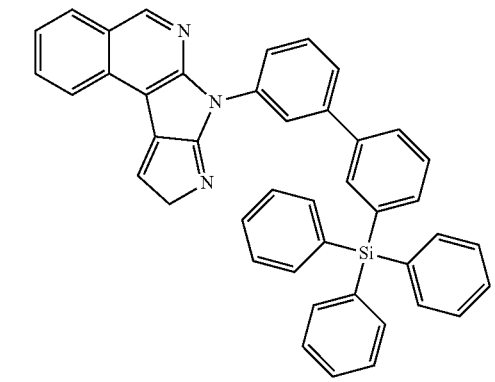
39
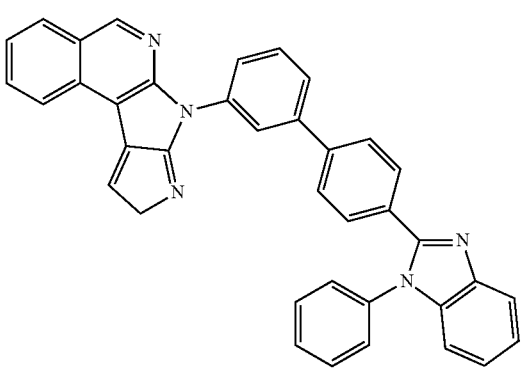
40
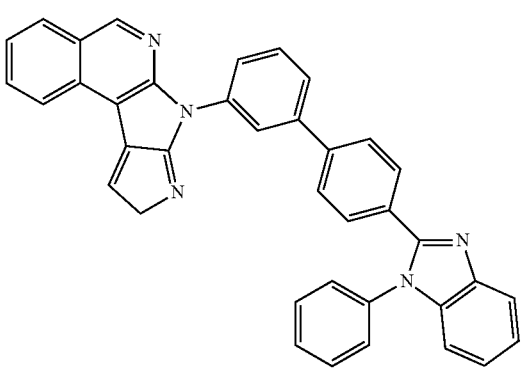
41
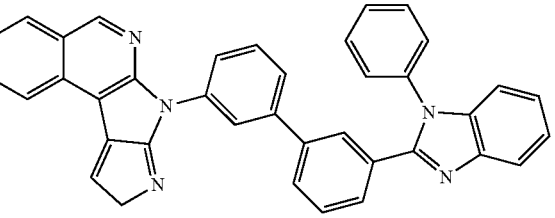
42
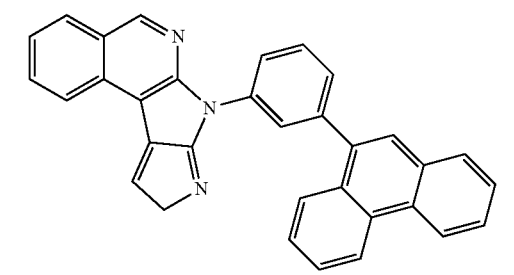

43

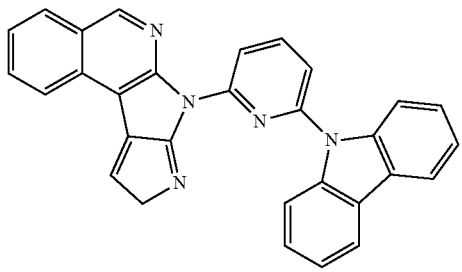

44

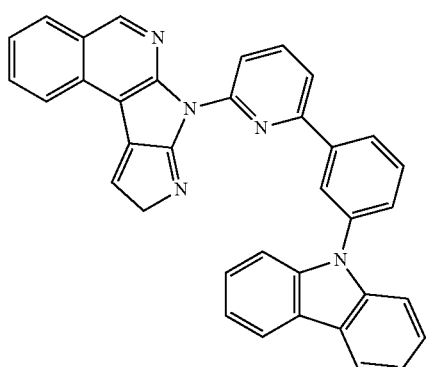

45

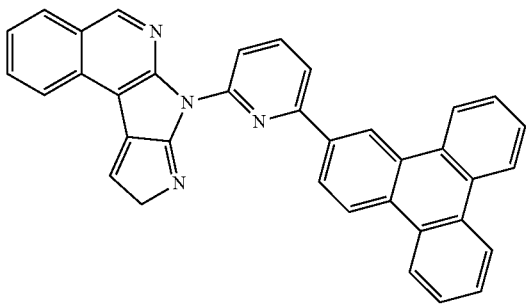

46

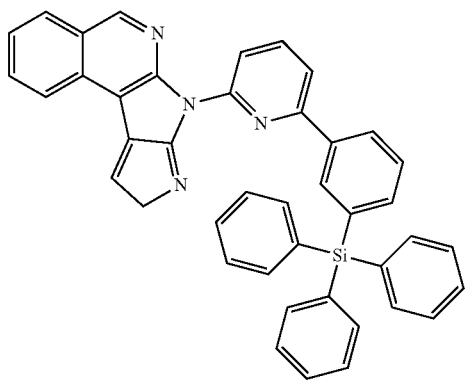

47

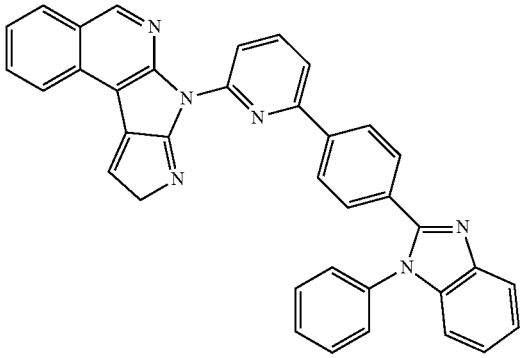

48

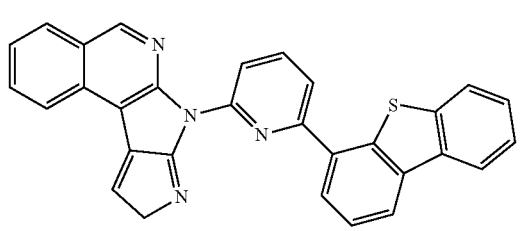

The heterocyclic compound represented by Formula 1 has a backbone with rigid quad rings including a heteroring

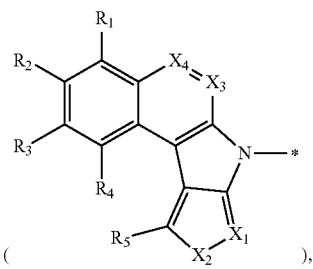

and a functional group $Ar_1$ (such as a phenanthrenyl group, a triphenylenyl group, a carbazolyl group, a benzoimidazolyl group, a dibenzothiophenyl group, or a tetraphenylsilanyl group) is bound to the backbone via a linking group $L_1$. Due to this structure, the heterocyclic compound has a high glass transition temperature Tg and a high melting point.

An organic light-emitting diode including the heterocyclic compound represented by Formula 1 has good heat resistance against Joule's heat generated between organic layers, within the organic layers, and/or between an emission layer and a metal electrode while stored and/or driven. Thus, the organic light-emitting diode including the heterocyclic compound maintains thermal stability at high temperatures over time, and thereby has high durability and a long lifetime.

The heterocyclic compound represented by Formula 1 may be synthesized using known organic synthesis methods. The method of synthesizing the heterocyclic compound would be known to those of ordinary skill in the art, especially with reference to the examples presented below.

The heterocyclic compound of Formula 1 may be disposed between a pair of electrodes of an organic light-emitting diode. For example, the heterocyclic compound may be used in an emission layer (EML), a layer between the EML and an anode (e.g., a hole injection layer (HIL), a hole transport layer (HTL), or a functional layer having both hole injecting and hole transporting capabilities), and/or a layer between a cathode and the EML (e.g., an electron injection layer (EIL), an electron transport layer (ETL), or a functional layer having both electron injecting and electron transporting capabilities).

An organic light-emitting diode according to another embodiment of the present invention includes a first electrode, a second electrode disposed opposite to the first electrode, and an organic layer between the first electrode and the second electrode. The organic layer includes the heterocyclic compound represented by Formula 1.

The term "organic layer," as used herein, refers to a single layer and/or multiple layers disposed between the first and second electrodes of an organic light-emitting diode.

As used herein, "the organic layer includes the heterocyclic compound represented by Formula 1" may be interpreted as "the organic layer includes at least one of the heterocyclic compounds represented by Formula 1, or at least two types of heterocyclic compounds represented by Formula 1."

The organic layer may include at least one layer selected from a HIL, a HTL, a functional layer having both hole injecting and hole transporting capabilities, a buffer layer, an electron blocking layer (EBL), an EML, a hole blocking layer (HBL), an ETL, an EIL, and a functional layer having both electron injecting and electron transporting capabilities.

The organic layer may include at least one of the HIL, the HTL, and the functional layer having both hole injecting and hole transporting capabilities, and at least one of the HIL, the HTL, and the functional layer having both hole injecting and hole transporting capabilities may include the heterocyclic compound.

The organic layer may include at least one of the EIL, the ETL, and the functional layer having both electron injecting and electron transporting capabilities, and at least one of the EIL, the ETL, and the functional layer having both electron injecting and electron transporting capabilities may include the heterocyclic compound.

The organic layer may include an EML that includes the heterocyclic compound.

The heterocyclic compound of Formula 1 contained in the EML may be used as a phosphorescent host. The heterocyclic compound contained in the EML may function as a phosphorescent host emitting red, green, or blue light, for example, green light.

The organic light-emitting diode and a method of manufacturing the organic light-emitting diode according to an embodiment of the present invention are described with reference to FIG. 1, but are not limited thereto, and various modifications may be made thereto.

FIG. 1 is a schematic cross-sectional view of an organic light-emitting diode according to an embodiment of the present invention.

The substrate 11 (which may be any substrate commonly used in organic light-emitting diodes) may be a glass substrate or a transparent plastic substrate with good mechanical strength, thermal stability, transparency, surface smoothness, ease of handling, and waterproofness.

A first electrode 13 may be formed on the substrate 11 by depositing or sputtering a material used to form the first electrode 13. When the first electrode 13 is an anode, the material used to form the first electrode 13 may be a high work-function material so as to facilitate hole injection. The first electrode 13 may be a reflective electrode or a transmissive electrode. Transparent and conductive materials such as indium tin oxide (ITO), indium zinc oxide (IZO), tin oxide ($SnO_2$), and zinc oxide (ZnO) may be used to form the first electrode 13. The first electrode 13 may be formed as a reflective electrode using magnesium (Mg), silver (Ag), aluminum (Al), aluminum-lithium (Al—Li), calcium (Ca), silver-indium tin oxide (Ag:ITO), magnesium-indium (Mg—In), magnesium-silver (Mg—Ag), or the like. The first electrode 13 may have a single-layered or a multi-layered structure. For example, the first electrode 13 may have a triple-layered structure of ITO/Ag/ITO, but is not limited thereto.

An organic layer 15 is formed on the first electrode 13. The organic layer 15 may include a HIL (not shown), a HTL (not shown), a buffer layer (not shown), an EML 16, an ETL (not shown), and an EIL (not shown).

The HIL may be formed on the first electrode 13 by vacuum deposition, spin coating, casting, Langmuir-Blodgett (LB) deposition, or the like. When the HIL is formed using vacuum deposition, the deposition conditions may vary according to the compound used to form the HIL and the structural and thermal characteristics of the HIL to be formed. For example, the deposition conditions may include a deposition temperature of about 100 to about 500° C., a vacuum pressure of about $10^{-8}$ to about $10^{-3}$ torr, and a deposition rate of about 0.01 to about 100 Å/sec, but are not limited thereto. When the HIL is formed using spin coating, the coating conditions may vary according to the compound used to form the HIL and the structural and thermal properties of the HIL to be formed. For example, the coating conditions may include a coating speed of about 2000 rpm to about 5000 rpm, and a thermal treatment temperature of about 80° C. to about 200° C., where the thermal treatment is used to remove solvent after coating. However, the coating conditions are not limited thereto. The hole injecting materials may include at least one of the heterocyclic compound of Formula 1 and known hole injecting materials. Examples of known materials that may be used to form the HIL include, but are not limited to, N,N'-diphenyl-N,N'-bis-[4-(phenyl-m-tolyl-amino)-phenyl]-biphenyl-4,4'-diamine (DNTPD), phthalocyanine compounds such as copper phthalocyanine, 4,4',4"-tris (3-methylphenylphenylamino)triphenylamine (m-MTDATA), N,N'-di(1-naphthyl)-N,N'-diphenylbenzidine (NPB), TDATA, 2T-NATA, polyaniline/dodecylbenzenesulfonic acid (Pani/DBSA), poly(3,4-ethylenedioxythiophene)/poly(4-styrenesulfonate) (PEDOT/PSS), polyaniline/camphor sulfonicacid (Pani/CSA), and polyaniline)/poly(4-styrenesulfonate (PANI/PSS). The thickness of the HIL may be about 100 to about 10,000 Å, and for example, about 100 to about 1,000 Å. When the thickness of the HIL is within these ranges, the HIL may have good hole injecting ability without substantially increasing the driving voltage.

Then, the HTL may be formed on the HIL by vacuum deposition, spin coating, casting, LB deposition, or the like. When the HTL is formed by vacuum deposition or spin coating, the conditions for deposition or coating may be similar to those used in forming the HIL. However, the conditions for deposition or coating may vary according to the material used to form the HTL. The hole transporting materials may include at least one of the heterocyclic compound of Formula 1 and known hole transporting materials. Examples of known hole transporting material include, but are not limited to, carbazole derivatives such as N-phenylcarbazole and polyvinyl carbazole, N,N'-bis(3-methylphenyl)-N,N'-diphenyl-[1,1-biphenyl]-4,4'-diamine (TPD), 4,4',4"-tris(N-carbazolyl)triphenylamine (TCTA), and N,N'-di(1-naphthyl)-N,N'-diphenylbenzidine (NPB). The thickness of the HTL may be about 50 to about 2,000 Å, for example, about 100 to about 1,500 Å. When the thickness of the HTL is within these ranges, the HTL may have good hole transporting ability without substantially increasing the driving voltage The functional layer having both hole injecting and hole transporting capabilities may include at least one of the heterocyclic compound of Formula 1, a hole injecting material, and a hole transporting material. The thickness of the functional layer having both hole injecting and hole transporting capabilities may be about 500 Å to about 10,000 Å, for example, about 100 Å to about 1,000 Å. When the thickness of the functional layer having both hole injecting and hole transporting capabilities is within these ranges, the functional layer having both hole injecting and hole transporting capabilities may have good hole injecting and hole transporting abilities without a substantially increasing the driving voltage.

At least one of the HIL, the HTL, and the functional layer having both hole injecting and hole transporting capabilities may further include a charge-generating material in order to improve conductivity, or the like, in addition to at least one of the heterocyclic compound of Formula 1, known hole injecting materials, and known hole transporting materials.

A buffer layer may be disposed between the EML 16 and at least one of the HIL, the HTL, and the functional layer having both hole injecting and hole transporting capabilities. The buffer layer may increase efficiency by compensating for an optical resonant distance according to the wavelength of light emitted from the EML 16. The buffer layer may include known hole injecting materials and known hole transporting materials.

The EML 16 may be formed on the HTL, the functional layer having both hole injecting and hole transporting capa- bilities, or the buffer layer by vacuum deposition, spin coating, casting, LB deposition, or the like. When the EML 16 is formed by vacuum deposition or spin coating, the deposition and coating conditions may be similar to those used in forming the HIL. However, the deposition and coating conditions may vary according to the compound used to form the EML 16.

The heterocyclic compound of Formula 1 may be used as a host material of the EML 16. Alternatively, known host materials other than the heterocyclic compound of Formula 1 may be used. The host material may include, but is not limited to, Alq3, 4,4'-biscarbazolylbiphenyl (CBP), poly(n-vinylcarbazole) (PVK), 9,10-di(naphthalene-2-yl)anthracene (ADN), TCTA, 1,3,5-tris(N-phenylbenzimidazole-2-yl)benzene) (TPBI), 3-tert-butyl-9,10-di(naphth-2-yl)anthracene (TBADN), E3, distyrylarylene (DSA), or dmCBP.

If the organic light-emitting diode 10 includes at least one of a red EML, a green EML, and a blue EML, the EML 16 may include at least one of the following dopants (ppy=phenylpyridine):

The following compounds may be used as a blue dopant, but the blue dopant is not limited thereto.

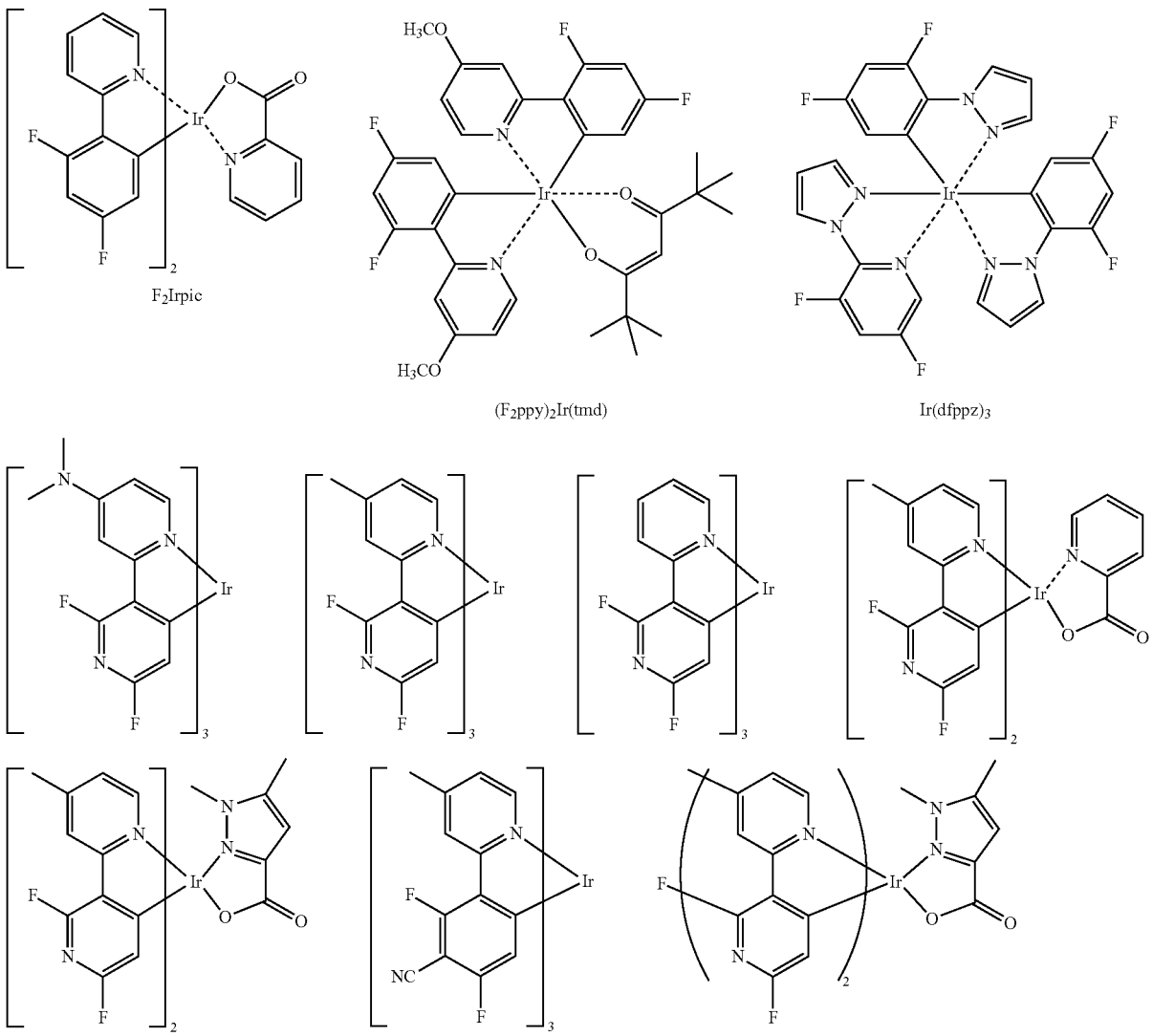

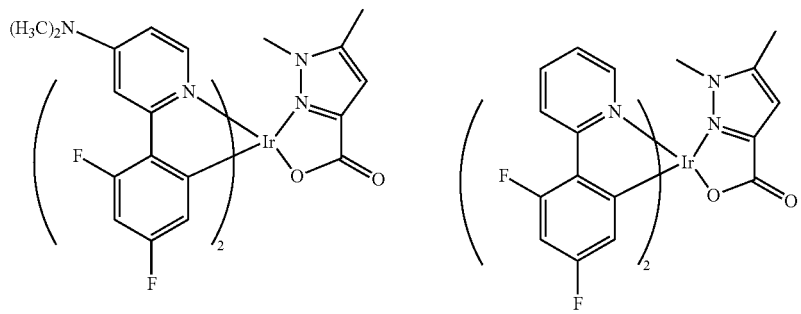
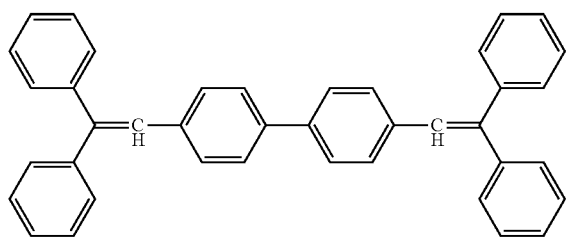
DPVBi
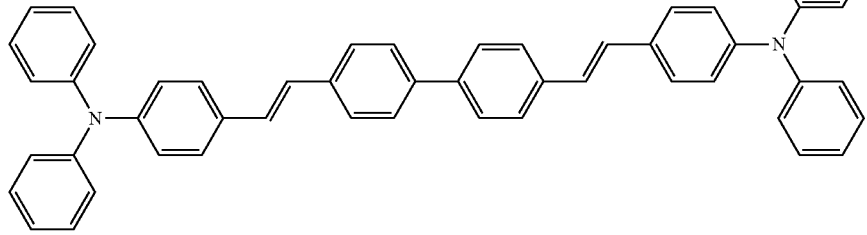
DPAVBi
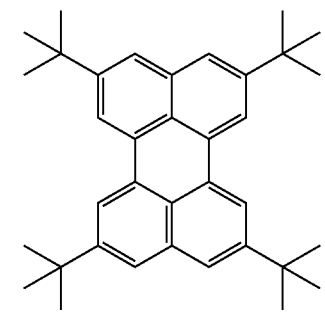
TBPe
The following compounds may be used as a red dopant, but the red dopant is not limited thereto.
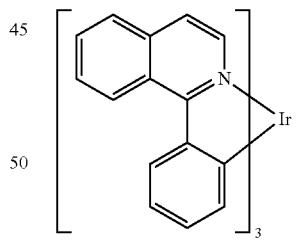
Ir(piq)₃
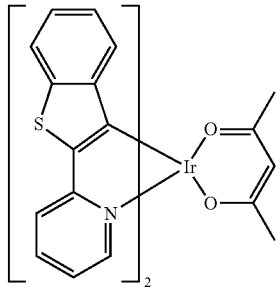
Btp₂Ir(acac)
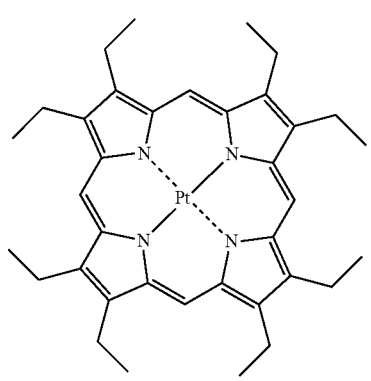
PtOEP
-continued
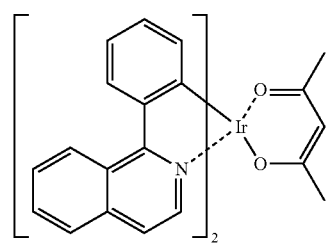

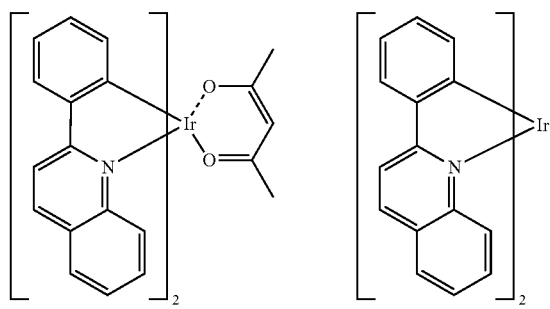
Ir(pq)₂(acac)     Ir(2-phq)₃
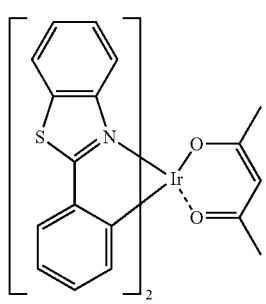
Ir(BT)₂(acac)
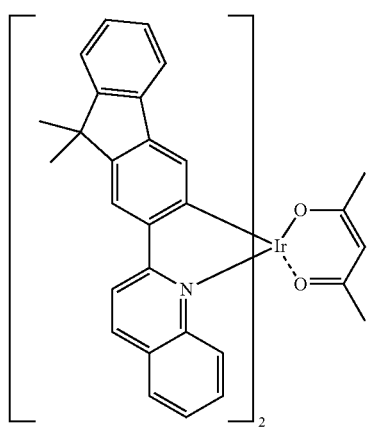
Ir(flq)₂(acac)
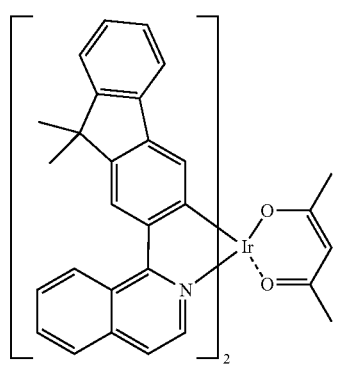
Ir(fliq)₂(acac)
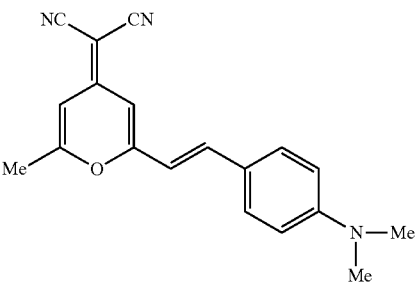
DCM
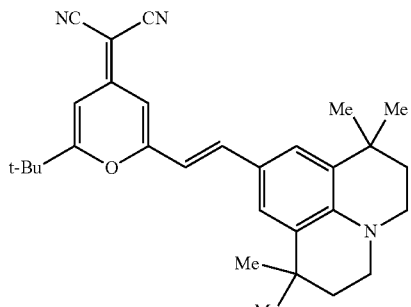
DCJTB
The following compounds may be used as a green dopant, but the green dopant is not limited thereto.
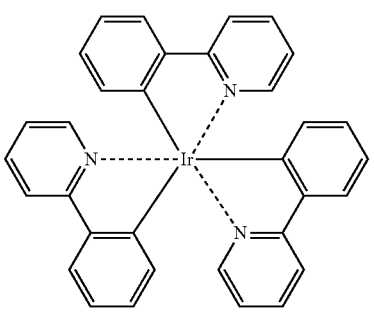
Ir(ppy)₃
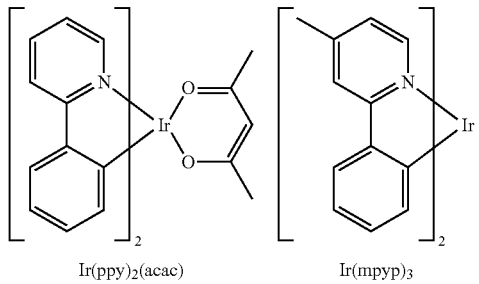
Ir(ppy)₂(acac)     Ir(mpyp)₃

-continued

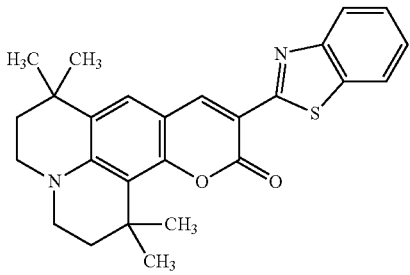

C545T

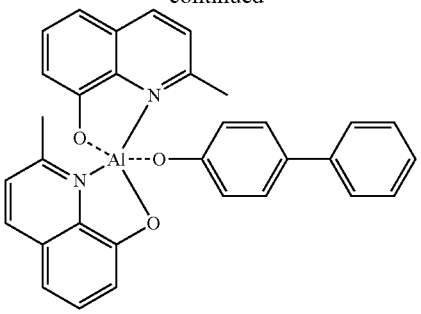

BAlq

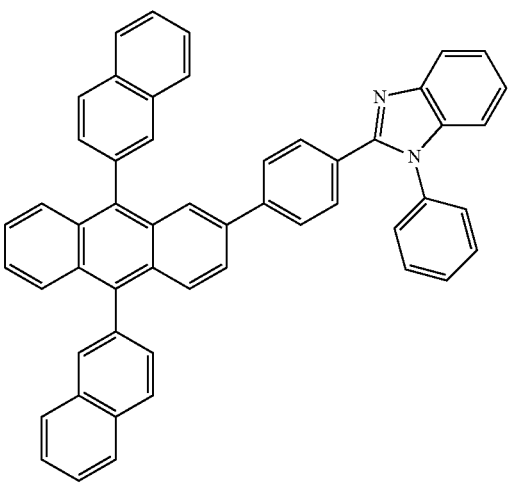

Compound 201

Compound 202

In addition, the dopant of the EML 16 may include a Pt-complex, a Os-complex, or the like, but is not limited thereto.

If the EML 16, and at least one of the EIL, the ETL, and the functional layer having both electron injecting and electron transporting capabilities of the organic light-emitting diode 10 include the heterocyclic compound of Formula 1, the EML may include a known arylamine compound.

If the EML 16 includes a host and a dopant, the amount of the dopant may be about 0.01 to about 15 parts by weight based on 100 parts by weight of the host, but is not limited thereto.

The thickness of the EML 16 may be about 100 Å to about 1000 Å, for example, about 200 Å to about 600 Å. When the thickness of the EML 16 is within these ranges, the EML 16 may have good light emitting ability without substantially increasing the driving voltage.

Then, the ETL may be formed on the EML 16 by vacuum deposition, spin coating, casting, or the like. When the ETL is formed by vacuum deposition or spin coating, the deposition and coating conditions may be similar to those used in forming the HIL. However, the deposition and coating conditions may vary according to the compound used to form the ETL. An electron transporting material may include at least one of the heterocyclic compound of Formula 1 and any known electron transporting material that stably transports electrons injected from the cathode. Examples of known electron transporting materials include, but are not limited to, quinoline derivatives, such as tris-(8-hydroxyquinoline) aluminum (Alq3), TAZ, Balq, beryllium bis(benzoquinolin-10-olate) (Balq2), ADN, Compound 201, and Compound 202.

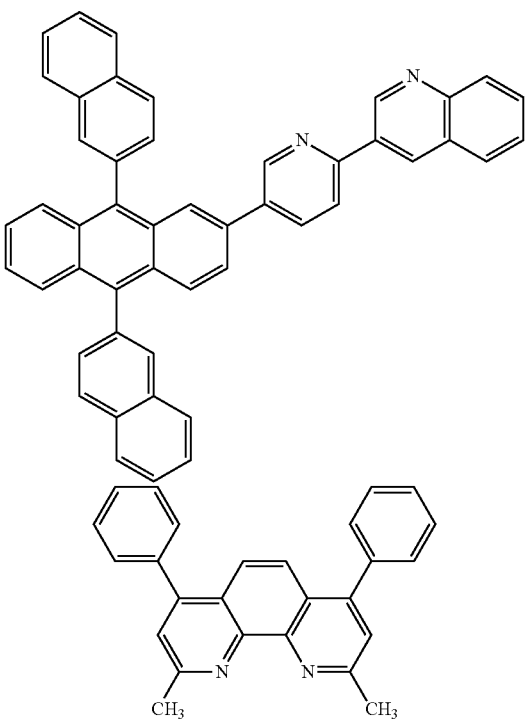

TAZ

BCP

The thickness of the ETL may be about 100 Å to about 1,000 Å, for example, about 150 Å to about 500 Å. When the thickness of the ETL is within these ranges, the ETL may have good electron transporting ability without substantially increasing the driving voltage.

Alternatively, the ETL may further include a metal complex in addition to the heterocyclic compound and known electron transporting materials. Examples of the metal complex include Li complexes, such as lithium quinolate (LiQ) or Compound 203 below.

Compound 203

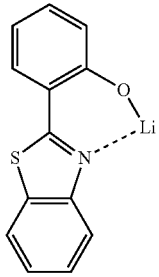

In addition, the EIL, which facilitates injection of electrons from the cathode, may be formed on the ETL. Examples of electron injecting materials include LIF, NaCl, CsF, $Li_2O$, and BaO. The conditions for deposition of the EIL are similar to those used in forming the HIL. However, the deposition conditions may vary according to the material used to form the EIL. The thickness of the EIL may be about 1 to about 100 Å, for example, about 3 to about 90 Å. When the thickness of the EIL is within these ranges, the EIL may have good electron injecting ability without substantially increasing the driving voltage.

The second electrode 19 is formed on the organic layer 15. The second electrode 19 may be a cathode, which is an electron injecting electrode. A material for forming the second electrode 19 may be a metal, an alloy, an electrically conductive compound (which have low-work functions), or a mixture thereof. For example, the second electrode 19 may be a transmissive electrode formed of lithium (Li), magnesium (Mg), aluminum (Al), an Al:Li alloy, calcium (Ca), a Mg:In alloy, or a Mg:Ag alloy as a thin film. Meanwhile, in order to manufacture a top-emission type organic light-emitting diode, a transmissive electrode formed of ITO or IZO may be used, and various modifications may be made thereto.

When a phosphorescent dopant is also used to form the EML 16, a HBL may be formed between the HTL and the EML 16 or between the functional layer having both hole injecting and hole transporting capabilities and the EML 16 by vacuum deposition, spin coating, casting, LB deposition, or the like, in order to prevent diffusion of triplet excitons or holes into the ETL. When the HBL is formed by vacuum deposition or spin coating, the conditions for deposition and coating may be similar to those used in forming the HIL. However, the conditions for deposition and coating may vary according to the material used to form the HBL. Any known hole blocking material commonly used in the art may be used. Examples of hole blocking materials include, but are not limited to, oxadiazole derivatives, triazole derivatives, and phenanthroline derivatives. For example, BCP may be used as the hole blocking material.

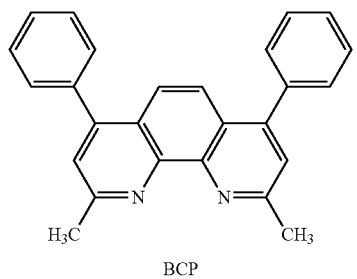 [SMILES: Cc1cc(-c2ccccc2)c2ccc3c(-c4ccccc4)cc(C)nc3c2n1 ; "BCP"]

BCP

The thickness of the HBL may be about 20 to about 1,000 Å, for example, about 30 to about 300 Å. When the thickness of the HBL is within these ranges, the HBL may have good hole blocking ability without substantially increasing the driving voltage.

According to another embodiment of the present invention, a flat panel display device includes an organic light-emitting diode having the heterocyclic compound represented by Formula 1. The flat panel display device includes an organic light-emitting diode and a transistor. The transistor includes a source, a drain, a gate, and an active layer. The first electrode of the organic light-emitting diode is electrically connected to one of the source or the drain of the transistor. The active layer of the transistor may be an amorphous silicon layer, a crystalline silicon layer, an organic semiconductor layer, an oxide semiconductor layer, or the like.

Examples of the unsubstituted $C_1$-$C_{30}$ alkyl group (or $C_1$-$C_{30}$ alkyl group) include linear or branched alkyl groups such as methyl, ethyl, propyl, isobutyl, sec-butyl, pentyl, iso-amyl, and hexyl. The substituted $C_1$-$C_{30}$ alkyl group is obtained by substituting at least one hydrogen atom of the unsubstituted $C_1$-$C_{30}$ alkyl group with a heavy hydrogen atom, a halogen atom, a hydroxyl group, a nitro group, a cyano group, an amino group, an amidino group, hydrazine, hydrazone, a carboxyl group or a salt thereof, a sulfonic acid group or a salt thereof, a phosphoric acid group or a salt thereof, a $C_1$-$C_{30}$ alkyl group, a $C_2$-$C_{30}$ alkenyl group, a $C_2$-$C_{30}$ alkynyl group, a $C_6$-$C_{30}$ aryl group, a $C_2$-$C_{30}$ heteroaryl group, —$N(Q_{11})(Q_{12})$, or $Si(Q_{13})(Q_{14})(Q_{15})(Q_{16})$-, where $Q_{11}$ to $Q_{16}$ are each independently a hydrogen atom, a $C_1$-$C_{30}$ alkyl group, a $C_2$-$C_{30}$ alkenyl group, a $C_2$-$C_{30}$ alkynyl group, a $C_5$-$C_{30}$ aryl group, or a $C_2$-$C_{30}$ heteroaryl group.

The unsubstituted $C_1$-$C_{30}$ alkoxy group (or $C_1$-$C_{30}$ alkoxy group) may be represented by —OA, where A is an unsubstituted $C_1$-$C_{30}$ alkyl group. Examples of the $C_1$-$C_{30}$ alkoxy group include methoxy, ethoxy, and isopropyloxy. The substituted $C_1$-$C_{30}$ alkoxy group is obtained by substituting at least one hydrogen atom of the $C_1$-$C_{30}$ alkoxy group with one of the substituent groups described above with respect to the $C_1$-$C_{30}$ alkyl group.

The unsubstituted $C_2$-$C_{30}$ alkenyl group (or $C_2$-$C_{30}$ alkenyl group) refers to a hydrocarbon chain having at least one carbon-carbon double bond within or at a terminal end of the unsubstituted $C_2$-$C_{30}$ alkyl group. Examples of the $C_2$-$C_{30}$ alkenyl group include ethenyl, propenyl, and butenyl. The substituted $C_2$-$C_{30}$ alkenyl group is obtained by substituted at least one hydrogen atom in the $C_2$-$C_{30}$ alkenyl group with one of the substituent groups described above with respect to the $C_1$-$C_{30}$ alkyl group.

The unsubstituted $C_2$-$C_{30}$ alkynyl group (or $C_2$-$C_{30}$ alkynyl group) refers to a hydrocarbon chain having at least one carbon-carbon triple bond within or at a terminal end of the $C_2$-$C_{30}$ alkyl group. Examples of the $C_2$-$C_{30}$ alkynyl group include ethynyl and propynyl. The substituted $C_2$-$C_{30}$ alkynyl group is obtained by substituting at least one hydrogen atom of the $C_2$-$C_{30}$ alkynyl group with one of the substituent groups described above with respect to the $C_1$-$C_{30}$ alkyl group.

The unsubstituted $C_5$-$C_{30}$ aryl group refers to a monovalent group having a $C_5$-$C_{30}$ carbocyclic aromatic system including at least one aromatic ring. The unsubstituted $C_5$-$C_{30}$ arylene group refers to a divalent group having a $C_5$-$C_{30}$ carbocyclic aromatic system including at least one aromatic ring. If the aryl group and the arylene group include at least two rings, the rings may be fused to each other. The substituted $C_5$-$C_{30}$ aryl group is prepared by substituting at least one hydrogen atom in the $C_5$-$C_{30}$ aryl group with one of the substituent groups described above with respect to the $C_1$-$C_{30}$ alkyl group. The substituted $C_5$-$C_{30}$ arylene group is prepared by substituting at least one hydrogen atom in the $C_5$-$C_{30}$ arylene group with one of the substituent groups described above with respect to the $C_1$-$C_{30}$ alkyl group.

The unsubstituted $C_2$-$C_{30}$ heteroaryl group is a monovalent group having at least one aromatic ring having at least one heteroatom selected from N, O, P, and S. The unsubstituted $C_2$-$C_{30}$ heteroarylene group is a divalent group having at least one aromatic ring having at least one heteroatom selected from N, O, P, and S.

When the heteroaryl group and the heteroarylene group have at least two rings, they may be fused to each other. The substituted $C_2$-$C_{30}$ heteroaryl group is prepared by substituting at least one hydrogen atom in the $C_2$-$C_{30}$ heteroaryl group with one of the substituent groups described above with respect to the $C_1$-$C_{30}$ alkyl group. The substituted $C_2$-$C_{30}$ heteroarylene group is prepared by substituting at least one hydrogen atom in the $C_2$-$C_{30}$ heteroarylene group with one of the substituent groups described above with respect to the $C_1$-$C_{30}$ alkyl group.

The substituted or unsubstituted $C_5$-$C_{30}$ aryloxy group is represented by —$OA_2$, where $A_2$ is a substituted or unsubstituted $C_5$-$C_{30}$ aryl group. The substituted or unsubstituted $C_5$-$C_{30}$ arylthio group is represented by —$SA_3$, wherein $A_3$ is a substituted or unsubstituted $C_3$-$C_{60}$ aryl group.

Hereinafter, one or more embodiments will be described with reference to the following examples. These examples are presented for illustrative purposes only, and do not limit the purpose and scope of the one or more embodiments of the present invention.

First, Intermediates A and B were synthesized according to the following reaction mechanism.

Synthesis of Intermediate A 20 g (1 eq, 0.092 mol) of 2-nitronaphthalen-1-yl boronic acid and 18.3 g (1.2 eq, 0.11 mol) of 3-bromothiophene were added to a flask, and 2.12 g (0.02 eq, 0.00184 mol) of Pd(PPh$_3$)$_4$ was added thereto. 550 Ml of toluene and 100 ml of a 2 M $K_2CO_3$ saturated solution were added thereto, and the mixture was refluxed while stirring for 5 hours.

After the reaction was terminated, the resultant was cleaned with 500 Ml of MC and 200 Ml of distilled water and subjected to extraction to obtain a solid. The solid was purified by column chromatography to obtain 18.81 g of Intermediate A (Yield: 80.1%). 1H NMR: 7.22 (d, 1H), 7.73 (m, 3H), 8.02 (m, 4H), 9.05 (s, 1H)

Synthesis of Intermediate B 20 g (1 eq, 0.078 mol) of Compound B, 120 g (800 mmol) of SnCl$_2$ 2H$_2$O, 600 mL of acetic acid, and 70 mL of 1N HCl were added to a reactor, and the mixture was stirred at 80° C. overnight. A solvent was distilled under reduced pressure, and the reaction mixture was dissolved in a mixture of THF and EA. Then, the resultant was cleaned with a NaHCO$_3$ aqueous solution and brine. Moisture was removed using anhydrous MgSO$_4$, and the resultant was subjected to distillation under reduced pressure and recrystallized using MeOH to obtain 8.2 g of Intermediate B (Yield: 47%). 1H NMR: 7.2 (s, 2H), 7.67 (m, 4H), 8.16 (t, 1H), 8.54 (t, 1H), 10.1 (S, 1H NH)

Synthesis of Compound 1

10 g (1 eq, 0.044 mol) of Intermediate B and 15.87 g (1.1 eq, 0.049 mol) of 9-(3-bromophenyl)-9H-carbazole were added to a flask and dissolved in 1200 Ml of toluene. 0.86 g (0.02 eq, 0.0008 mmol) of Pd$_2$(dba)$_3$, 6.75 g (1.2 eq, 0.0528 mol) of Na(t-bu)O, and 0.28 g (0.08 ea, 0.0035 mmol) of P(t-Bu)$_3$ were added thereto, and the mixture was stirred while heating for 12 hours. After the reaction was terminated, the reaction solution was filtered using celite and purified by column chromatography to obtain 14.7 g of Compound 1 (Yield: 72%).

Elemental Analysis for $C_{32}H_{20}N_2S$: calcd C, 82.73; H, 4.34; N, 6.03; S, 6.90

HRMS for $C_{32}H_{20}N_2S$ [M]$^+$: calcd 464, found 463.

Synthesis of Compound 3

10 g (1 eq, 0.044 mol) of Intermediate B and 19.51 g (1.1 eq, 0.049 mol) of 9-(4-bromobiphenyl-3-yl)-9H-carbazole were added to a flask and dissolved in 1200 Ml of toluene. 0.86 g (0.02 eq, 0.0008 mmol) of Pd$_2$(dba)$_3$, 6.75 g (1.2 eq, 0.0528 mol) of Na(t-bu)O, and 0.28 g (0.08 ea, 0.0035 mmol) of P(t-Bu)$_3$ were added thereto, and the mixture was

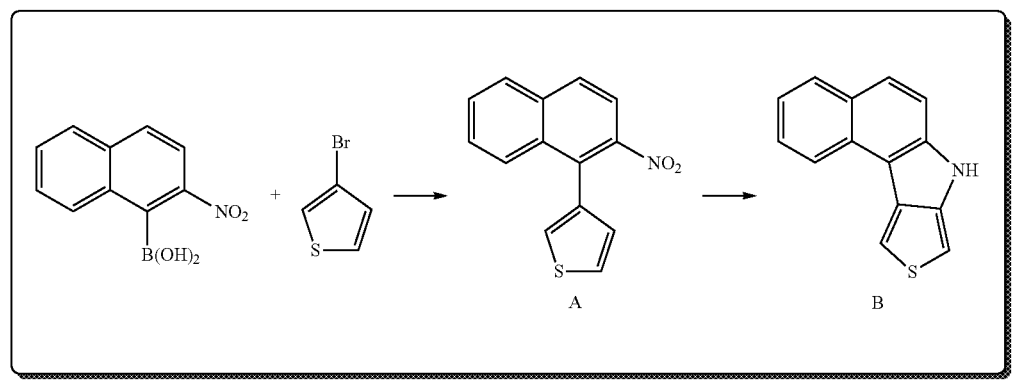

stirred while heating for 12 hours. After the reaction was terminated, the reaction solution was filtered using celite and purified by column chromatography to obtain 16.77 g of Compound 3 (Yield: 70.5%).

Elemental Analysis for $C_{38}H_{24}N_2S$: calcd C, 84.41; H, 4.47; N, 5.18; S, 5.93;

HRMS for $C_{38}H_{24}N_2S$ [M]$^+$: calcd 540, found 539.

Synthesis of Compound 5

10 g (1 eq, 0.044 mol) of Intermediate B and 21.62 g (1.1 eq, 0.049 mol) of (3'-bromobiphenyl-3-yl)triphenylsilane were added to a flask and dissolved in 1200 M of toluene. 0.86 g (0.02 eq, 0.0008 mmol) of $Pd_2(dba)_3$, 6.75 g (1.2 eq, 0.0528 mol) of Na(t-bu)O, and 0.28 g (0.08 ea, 0.0035 mmol) of $P(t-Bu)_3$ were added thereto, and the mixture was stirred while heating for 12 hours. After the reaction was terminated, the reaction solution was filtered using celite and purified by column chromatography to obtain 21.14 g of Compound 5 (Yield: 75.8%).

Elemental Analysis for $C_{44}H_{31}NSSi$: calcd C C, 83.37; H, 4.93; N, 2.21; S, 5.06; Si, 4.43

HRMS for $C_{44}H_{31}NSSi$ [M]$^+$: calcd 633, found 632.

Synthesis of Compound 8

10 g (1 eq, 0.044 mol) of Intermediate B and 20.84 g (1.1 eq, 0.049 mol) of 2-(3'-bromobiphenyl-3-yl)-1-phenyl-1H-benzo[d]imidazole were added to a flask and dissolved in 1200 Ml of toluene. 0.86 g (0.02 eq, 0.0008 mmol) of $Pd_2(dba)_3$, 6.75 g (1.2 eq, 0.0528 mol) of Na(t-bu)O, and 0.28 g (0.08 ea, 0.0035 mmol) of $P(t-Bu)_3$ were added thereto, and the mixture was stirred while heating for 12 hours. After the reaction was terminated, the reaction solution was filtered using celite and purified by column chromatography to obtain 20.0 g of Compound 8 (Yield: 80.1%).

Elemental Analysis for $C_{39}H_{25}N_3S$: calcd C, 82.51; H, 4.44; N, 7.40; S, 5.65

HRMS for $C_{39}H_{25}N_3S$ [M]$^+$: calcd 567, found 566.

Synthesis of Compound 12

10 g (1 eq, 0.044 mol) of Intermediate B and 17.56 g (1.1 eq, 0.049 mol) of 9-(3-(6-bromopyridin-2-yl)phenyl)-9H-carbazole were added to a flask and dissolved in 1200 Ml of toluene. 0.86 g (0.02 eq, 0.0008 mmol) of $Pd_2(dba)_3$, 6.75 g (1.2 eq, 0.0528 mol) of Na(t-bu)O, and 0.28 g (0.08 ea, 0.0035 mmol) of $P(t-Bu)_3$ were added thereto, and the mixture was stirred while heating for 12 hours. After the reaction was terminated, the reaction solution was filtered using celite and purified by column chromatography to obtain 18.49 g of Compound 12 (Yield: 77.6%).

Elemental Analysis for $C_{37}H_{23}N_3S$: calcd C, 82.04; H, 4.28; N, 7.76; S, 5.92

HRMS for $C_{37}H_{23}N_3S$ [M]$^+$: calcd 541, found 540.

Synthesis of Compound 16

10 g (1 eq, 0.044 mol) of Intermediate B and 16.67 g (1.1 eq, 0.049 mol) of 2-bromo-6-(dibenzo[b,d]thiophen-4-yl)pyridine were added to a flask and dissolved in 1200 Ml of toluene. 0.86 g (0.02 eq, 0.0008 mmol) of $Pd_2(dba)_3$, 6.75 g (1.2 eq, 0.0528 mol) of Na(t-bu)O, and 0.28 g (0.08 ea, 0.0035 mmol) of $P(t-Bu)_3$ were added thereto, and the mixture was stirred while heating for 12 hours. After the reaction was terminated, the reaction solution was filtered using celite and purified by column chromatography to obtain 15.86 g of Compound 16 (Yield: 74.7%).

Elemental Analysis for $CO_{31}H_{18}N_2S_2$: calcd C, 77.15; H, 3.76; N, 5.80; S, 13.29

HRMS for $C_{31}H_{18}N_2S_2$ [M]$^+$: calcd 482, found 481.

Intermediates C, D, and E were synthesized according to the following reaction mechanism.

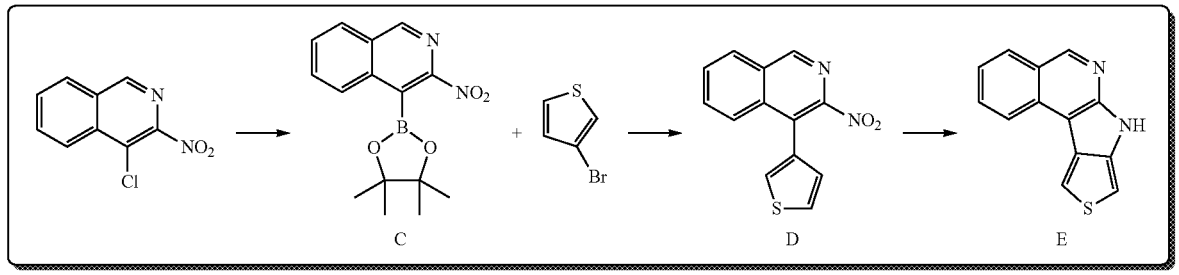

Synthesis of Intermediate C 50 g (1 eq, 0.239 mol) of 4-chloro-3-nitroisoquinoline, 4.2 g of $Pd(dppf)Cl_2$, 64.2 g (1.2 eq, 0.287 mol) of bis(pinacolate)diboron, and 38.8 g (4 eq 0.95 mol) of potassium acetate were dissolved in 500 mL of 1,4-dioxane. The reaction mixture was refluxed while stirring for 6 hours and subjected to extraction three times with dichloro methane and distilled water. The resultant was purified by column chromatography Hex:EA=9:1 (v:v)) to obtain 57.3 g of Intermediate C (Yield: 86%). 1H NMR: 8.56 (d, 1H), 7.81 (d, 1H) 7.55 (m, 5H), 7.30 (m, 3H), 7.28 (t, 1H), 7.21 (m, 2H), 1.26 (s, 12H)

Synthesis of Intermediate D 20 g (1 eq, 0.066 mol) of Intermediate C and 13 g (1.2 eq, 0.0799 mol) of 3-bromothiophene were added to a flask, and 1.52 g (0.02 eq, 0.0013 mol) of $Pd(PPh_3)_4$ was added thereto. 400 Ml of toluene and 100 ml of a 2 M $K_2CO_3$ saturated solution were added thereto, and the mixture was refluxed while stirring for 5 hours. After the reaction was terminated, the resultant was cleaned with 400 Ml of MC and 150 Ml of distilled water and subjected to extraction to obtain a solid. The solid was purified by column chromatography to obtain 14.2 g of Intermediate D (Yield: 84.5%). $^1$H NMR: 7.22 (d, 1H), 7.78 (m, 3H), 8.12 (m, 3H), 9.07 (s, 1H)

Synthesis of Intermediate E 30 g (1 eq, 0.117 mol) of Intermediate D, 150 g (0.1 mol) of $SnCl_2$ $2H_2O$, 600 mL of acetic acid, and 80 mL of 1N HCl were added to a reactor and the mixture was stirred at 80° C. overnight. The solvent was subjected to distillation at reduced pressure, and the reaction mixture was dissolved in a mixture of THF and EA and cleaned with a $NaHCO_3$ aqueous solution and brine. Moisture was removed using anhydrous $MgSO_4$, and the resultant was subjected to distillation under reduced pressure and recrystallized using MeOH to obtain 9.45 g of Intermediate E (Yield: 36%). $^1$H NMR: 7.27 (s, 2H), 7.67 (m, 5H), 8.91 (d, 1H)

Synthesis of Compound 19

10 g (1 eq, 0.044 mol) of Intermediate E and 17.75 g (1.1 eq, 0.049 mol) of 9-(3'-bromobiphenyl-4-yl)-9H-carbazole were added to a flask and dissolved in 900 Ml of toluene. 0.86 g (0.02 eq, 0.0008 mmol) of $Pd_2(dba)_3$, 6.75 g (1.2 eq, 0.0528 mol) of Na(t-bu)O, and 0.28 g (0.08 ea, 0.0035 mmol) of $P(t-Bu)_3$ were added thereto, and the mixture was stirred while heating for 12 hours. After the reaction was terminated, the reaction solution was filtered using celite and purified by column chromatography to obtain 19.7 g of Compound 19 (Yield: 82.8%).

Elemental Analysis for $C_{37}H_{23}N_3S$: calcd C, 82.04; H, 4.28; N, 7.76; S, 5.92

HRMS for $C_{37}H_{23}N_3S$ $[M]^+$: calcd 541, found 540.

Synthesis of Compound 24

10 g (1 eq, 0.044 mol) of Intermediate E and 20.8 g (1.1 eq, 0.049 mol) of 2-(3'-bromobiphenyl-3-yl)-1-phenyl-1H-benzo[d]imidazole were added to a flask and dissolved in 900 Ml of toluene. 0.86 g (0.02 eq, 0.0008 mmol) of $Pd_2(dba)_3$, 6.75 g (1.2 eq, 0.0528 mol) of Na(t-bu)O, and 0.28 g (0.08 ea, 0.0035 mmol) of $P(t-Bu)_3$ were added thereto, and the mixture was stirred while heating for 12 hours. After the reaction was terminated, the reaction solution was filtered using celite and purified by column chromatography to obtain 21.9 g of Compound 24 (Yield: 87.8%).

Elemental Analysis for $C_{38}H_{24}N_4S$: calcd C, 80.26; H, 4.25; N, 9.85; S, 5.64

HRMS for $C_{38}H_{24}N_4S$ $[M]^+$: calcd 568, found 567.

Synthesis of Compound 28

10 g (1 eq, 0.044 mol) of Intermediate E and 19.5 g (1.1 eq, 0.049 mol) of 9-(3-(6-bromopyridin-2-yl)phenyl)-9H-carbazole were added to a flask and dissolved in 900 Ml of toluene. 0.86 g (0.02 eq, 0.0008 mmol) of $Pd_2(dba)_3$, 6.75 g (1.2 eq, 0.0528 mol) of Na(t-bu)O, and 0.28 g (0.08 ea, 0.0035 mmol) of $P(t-Bu)_3$ were added thereto, and the mixture was stirred while heating for 12 hours. After the reaction was terminated, the reaction solution was filtered using celite and purified by column chromatography to obtain 19.3 g of Compound 28 (Yield: 81.1%).

Elemental Analysis for $C_{36}H_{22}N_4S$: calcd C, 79.68; H, 4.09; N, 10.32; S, 5.91

HRMS for $C_{36}H_{22}N_4S$ $[M]^+$: calcd 542, found 541.

Synthesis of Compound 30

10 g (1 eq, 0.044 mol) of Intermediate E and 21.6 g (1.1 eq, 0.049 mol) of 2-bromo-6-(3-(triphenylsilyl)phenyl)pyridine were added to a flask and dissolved in 900 Ml of toluene. 0.86 g (0.02 eq, 0.0008 mmol) of $Pd_2(dba)_3$, 6.75 g (1.2 eq, 0.0528 mol) of Na(t-bu)O, and 0.28 g (0.08 ea, 0.0035 mmol) of $P(t-Bu)_3$ were added thereto, and the mixture was stirred while heating for 12 hours. After the reaction was terminated, the reaction solution was filtered using celite and purified by column chromatography to obtain 22.1 g of Compound 30 (Yield: 79.4%).

Elemental Analysis for $C_{42}H_{29}N_3SSi$: calcd C, 79.33; H, 4.60; N, 6.61; S, 5.04; Si, 4.42

HRMS for $C_{42}H_{29}N_3SSi$ $[M]^+$: calcd 635, found 634.

EXAMPLE 1

An anode was prepared by cutting a Corning 15 $\Omega/cm^2$ (1200 Å) ITO glass substrate to a size of 50 mm×50 mm×0.7 mm, ultrasonically cleaning the glass substrate using isopropyl alcohol and pure water for 10 minutes each, and then irradiating with UV light for 30 minutes and exposing to ozone to clean. Then, the glass substrate was disposed in a vacuum deposition apparatus.

Then, 2-TNATA was vacuum deposited on the ITO glass substrate to form a HIL having a thickness of 600 Å, and then NPB was vacuum deposited on the HIL to form a HTL having a thickness of 300 Å.

$Ir(ppy)_3$ as a phosphorescent dopant and Compound I as a green phosphorescent host were simultaneously deposited on the HTL at a weight ratio of 87:13 to form a green EML with a thickness of 300 Å.

Then, Alq3 was vacuum deposited on the EML to form an ETL having a thickness of 300 Å.

Al was vacuum-deposited on the ETL to form a cathode with a thickness of 1200 Å, thereby completing the manufacture of an organic light-emitting diode.

EXAMPLE 2

An organic light-emitting diode was manufactured in the same manner as Example 1, except that Compound 3 was used instead of Compound 1 in forming the EML.

EXAMPLE 3

An organic light-emitting diode was manufactured in the same manner as Example 1, except that Compound 5 was used instead of Compound 1 in forming the EML.

EXAMPLE 4

An organic light-emitting diode was manufactured in the same manner as Example 1, except that Compound 8 was used instead of Compound 1 in forming the EML.

EXAMPLE 5

An organic light-emitting diode was manufactured in the same manner as Example 1, except that Compound 12 was used instead of Compound 1 in forming the EML.

EXAMPLE 6

An organic light-emitting diode was manufactured in the same manner as Example 1, except that Compound 16 was used instead of Compound 1 in forming the EML.

EXAMPLE 7

An organic light-emitting diode was manufactured in the same manner as Example 1, except that Compound 19 was used instead of Compound 1 in forming the EML.

EXAMPLE 8

An organic light-emitting diode was manufactured in the same manner as Example 1, except that Compound 24 was used instead of Compound 1 in forming the EML.

EXAMPLE 9

An organic light-emitting diode was manufactured in the same manner as Example 1, except that Compound 28 was used instead of Compound 1 in forming the EML.

EXAMPLE 10

An organic light-emitting diode was manufactured in the same manner as Example 1, except that Compound 30 was used instead of Compound 1 in forming the EML.

COMPARATIVE EXAMPLE 1

An organic light-emitting diode was manufactured in the same manner as Example 1, except that CBP was used instead of Compound 1 in forming the EML.

Evaluation Example

The driving voltage, light emission efficiency, color coordinates, brightness, and lifespan of the organic light-emitting diodes prepared according to Examples 1 to 10 and Comparative Example 1 were evaluated using a PR650 (Spectroscan) Source Measurement Unit (PhotoResearch), and the results are shown in Table 1 below.

TABLE 1

| | Driving voltage (V) | Light emission efficiency (cd/A) | Color coordinates | Brightness (cd/m$^2$) | T95 life-span (hr @ 100 mA/cm$^2$) |
|---|---|---|---|---|---|
| Example 1 | 3.6 | 70.5 | (0.32, 0.62) | 3,500 | 397 |
| Example 2 | 4.1 | 67.9 | (0.32, 0.63) | 3,500 | 332 |
| Example 3 | 4.5 | 67.7 | (0.33, 0.63) | 3,500 | 275 |
| Example 4 | 3.9 | 65.3 | (0.34, 0.61) | 3,500 | 259 |
| Example 5 | 3.7 | 68.7 | (0.33, 0.62) | 3,500 | 264 |
| Example 6 | 4.1 | 66.6 | (0.31, 0.60) | 3,500 | 247 |
| Example 7 | 3.8 | 72.4 | (0.32, 0.60) | 3,500 | 219 |
| Example 8 | 3.7 | 65.5 | (0.32, 0.62) | 3,500 | 337 |
| Example 9 | 3.7 | 60.7 | (0.30, 0.62) | 3,500 | 356 |
| Example 10 | 4.2 | 62.9 | (0.31, 0.65) | 3,500 | 287 |
| Comparative Example 1 | 5.1 | 51.2 | (0.32, 0.62) | 3,500 | 175 |

Referring to Table 1, the organic light-emitting diodes prepared according to Examples 1 to 10 have lower driving voltage, higher light emission efficiency, and longer lifespan than the organic light-emitting diode prepared according to Comparative Example 1.

Quantitatively, the organic light-emitting diodes prepared according to Examples 1 to 10 have about 20% lower driving voltage and about 20% higher light emission efficiency than the organic light-emitting diode prepared according to Comparative Example 1. Particularly, the lifespan of the organic light-emitting diodes prepared according to Examples 1 to 10 was about 50% longer than that of the organic light-emitting diode prepared according to Comparative Example 1. These characteristics may be due to the good thermal stability of the heterocyclic compound represented by Formula 1 used in the organic light emitting diodes according to Examples 1 to 10.

As described above, the heterocyclic compound according to one or more embodiments of the present invention has a high glass transition temperature and good thermal stability. As a result, the compound may be used as a host material to improve light emission efficiency and life-span characteristics.

The organic light-emitting diode including the heterocyclic compound according to one or more embodiments of the present invention has low driving voltage, high light emission efficiency, long life-span, and good power efficiency, so that power consumption may be reduced.

While the present invention has been illustrated and described with reference to certain exemplary embodiments, those of ordinary skill in the art would understand that various changes may be made to the described embodiments without departing from the spirit and scope of the present invention as defined by the following claims.

What is claimed is:
1. A heterocyclic compound, comprising a compound represented by Formula 1:

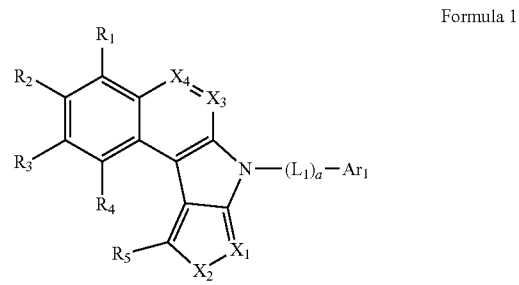

Formula 1 wherein:
$X_1$ comprises $CR_{11}$ or nitrogen (N),
$X_2$ comprises $C(R_{12})(R_{13})$, $NR_{14}$, S, or O,
each of $X_3$ and $X_4$ independently comprises $CR_{15}$ or N,
each of $R_1$ to $R_5$ and $R_{11}$ to $R_{15}$ independently comprises a hydrogen atom, a heavy hydrogen atom, a halogen atom, a hydroxyl group, a cyano group, a nitro group, an amino group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_5$-$C_{30}$ aryl group, or a substituted or unsubstituted $C_2$-$C_{30}$ heteroaryl group, $Ar_1$ comprises a halogen atom, a hydroxyl group, a cyano group, a nitro group, an amino group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_5$-$C_{30}$ aryl group, a substituted or unsubstituted $C_5$-$C_{30}$ aryloxy group, a substituted or unsubstituted $C_5$-$C_{30}$ arylthio group, a substituted or unsubstituted $C_2$-$C_{30}$ heteroaryl group, —N($Q_1$)($Q_2$), or —Si($Q_3$)($Q_4$)($Q_5$)($Q_6$), wherein:

each of $Q_1$ to $Q_6$ independently comprises a hydrogen atom, a heavy hydrogen atom, a halogen atom, a hydroxyl group, a cyano group, an amino group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_5$-$C_{30}$ aryl group, a substituted or unsubstituted $C_5$-$C_{30}$ aryloxy group, a substituted or unsubstituted $C_5$-$C_{30}$ arylthio group, or a substituted or unsubstituted $C_2$-$C_{30}$ heteroaryl group, $L_1$ comprises a substituted or unsubstituted $C_5$-$C_{30}$ arylene group or a substituted or unsubstituted $C_2$-$C_{30}$ heteroarylene group, and a is an integer from 1 to 3.

2. The heterocyclic compound of claim 1, wherein the compound represented by Formula 1 comprises a compound represented by Formula 2:

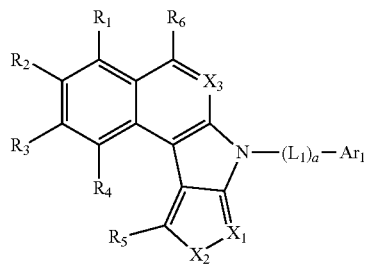

Formula 2 wherein:

each of $R_1$ to $R_6$ independently comprises a hydrogen atom, a heavy hydrogen atom, a halogen atom, a hydroxyl group, a cyano group, a nitro group, an amino group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_5$-$C_{30}$ aryl group, or a substituted or unsubstituted $C_2$-$C_{30}$ heteroaryl group.

3. The heterocyclic compound of claim 1, wherein the compound represented by Formula 1 comprises a compound represented by one of Formulae 3 to 6 below:

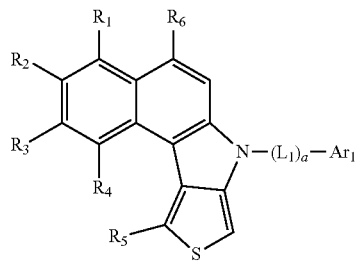

Formula 3

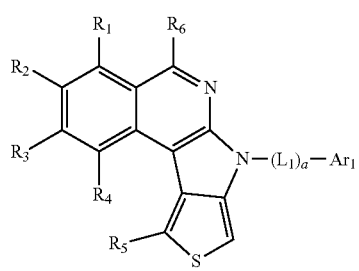

Formula 4

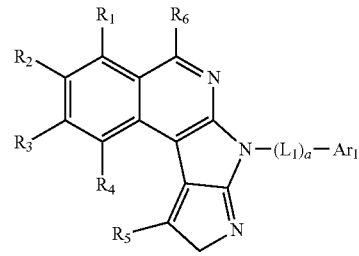

Formula 5

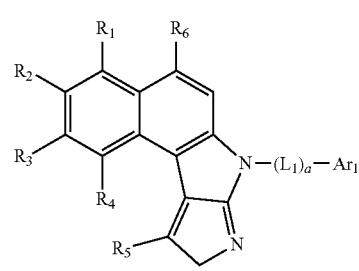

Formula 6 wherein:

each of $R_1$ to $R_6$ independently comprises a hydrogen atom, a heavy hydrogen atom, a halogen atom, a hydroxyl group, a cyano group, a nitro group, an amino group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_5$-$C_{30}$ aryl group, or a substituted or unsubstituted $C_2$-$C_{30}$ heteroaryl group.

4. The heterocyclic compound of claim 1, wherein each of $R_1$ to $R_5$ and $R_{11}$ to $R_{15}$ independently comprises a hydrogen atom, a heavy hydrogen atom, a substituted or unsubstituted $C_1$-$C_{30}$ alkyl group, a substituted or unsubstituted $C_5$-$C_{30}$ aryl group, or a substituted or unsubstituted $C_2$-$C_{30}$ heteroaryl group.

5. The heterocyclic compound of claim 1, wherein each of $R_1$ to $R_5$ and $R_{11}$ to $R_{15}$ independently comprises a hydrogen atom, a heavy hydrogen atom, a substituted or unsubstituted methyl group, a substituted or unsubstituted ethyl group, a substituted or unsubstituted propyl group, a substituted or unsubstituted butyl group, a substituted or unsubstituted phenyl group, a substituted or unsubstituted biphenyl group, a substituted or unsubstituted naphthyl group, or a substituted or unsubstituted anthryl group, a substituted or unsubstituted phenanthrenyl group, a substituted or unsubstituted pyrenyl group, a substituted or unsubstituted indolyl group, a substituted or unsubstituted indenyl group, a substituted or unsubstituted fluorenyl group, or a substituted or unsubstituted carbazolyl group.

6. The heterocyclic compound of claim 1, wherein $Ar_1$ comprises a substituted or unsubstituted $C_5$-$C_{30}$ aryl group, a substituted or unsubstituted $C_5$-$C_{30}$ aryloxy group, a substituted or unsubstituted $C_5$-$C_{30}$ arylthio group, a substituted or unsubstituted $C_2$-$C_{30}$ heteroaryl group, —N($Q_1$)($Q_2$), or —Si($Q_3$)($Q_4$)($Q_5$)($Q_6$), wherein each of $Q_1$ to $Q_6$ independently comprises a hydrogen atom, a heavy hydrogen atom, a substituted or unsubstituted $C_1$-$C_{30}$ alkyl group, a substituted or unsubstituted $C_5$-$C_{30}$ aryl group, or a substituted or unsubstituted $C_2$-$C_{30}$ heteroaryl group.

7. The heterocyclic compound of claim 1, wherein $Ar_1$ comprises a hydrogen atom, a heavy hydrogen atom, a substituted or unsubstituted $C_1$-$C_{20}$ alkyl group, a substituted or unsubstituted $C_1$-$C_{20}$ alkoxy group, a substituted or unsubstituted phenyl, a substituted or unsubstituted pentalenyl group, a substituted or unsubstituted indenyl group, a substituted or unsubstituted naphthyl group, a substituted or unsubstituted azulenyl group, a substituted or unsubstituted heptalenyl group, a substituted or unsubstituted indacenyl, a substituted or unsubstituted acenaphthyl group, a substituted or unsubstituted fluorenyl group, a substituted or unsubstituted spiro-fluorenyl group, a substituted or unsubstituted phenalenyl group, a substituted or unsubstituted phenanthrenyl group, a substituted or unsubstituted anthryl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentaphenyl group, a substituted or unsubstituted hexacenyl group, a substituted or unsubstituted pyrrolyl group, a substituted or unsubstituted imidazolyl group, a substituted or unsubstituted pyrazolyl group, a substituted or unsubstituted pyridinyl group, a substituted or unsubstituted pyrazinyl group, a substituted or unsubstituted pyrimidinyl group, a substituted or unsubstituted pyridazinyl group, a substituted or unsubstituted isoindolyl group, a substituted or unsubstituted indolyl group, a substituted or unsubstituted indazolyl group, a substituted or unsubstituted purinyl group, a substituted or unsubstituted quinolinyl group, a substituted or unsubstituted benzoquinolinyl group, a substituted or unsubstituted phthalazinyl group, a substituted or unsubstituted naphthyridinyl group, a substituted or unsubstituted quinoxalinyl group, a substituted or unsubstituted quinazolinyl group, a substituted or unsubstituted cinnolinyl group, a substituted or unsubstituted carbazolyl group, a substituted or unsubstituted phenanthridinyl group, a substituted or unsubstituted acridinyl group, a substituted or unsubstituted phenanthrolinyl group, a substituted or unsubstituted phenazinyl group, a substituted or unsubstituted benzooxazolyl group, a substituted or unsubstituted benzoimidazolyl group, a substituted or unsubstituted furanyl group, a substituted or unsubstituted benzofuranyl group, a substituted or unsubstituted thiophenyl group, a substituted or unsubstituted benzothiophenyl group, a substituted or unsubstituted thiazolyl group, a substituted or unsubstituted isothiazolyl group, a substituted or unsubstituted benzothiazolyl group, a substituted or unsubstituted isoxazolyl group, a substituted or unsubstituted oxazolyl group, a substituted or unsubstituted triazolyl group, a substituted or unsubstituted tetrazolyl group, a substituted or unsubstituted oxadiazolyl group, a substituted or unsubstituted triazinyl group, a substituted or unsubstituted dibenzopuranyl group, a substituted or unsubstituted dibenzothiophenyl group, a substituted or unsubstituted benzocarbazolyl group, or a substituted or unsubstituted tetraphenylsilanyl group.

8. The heterocyclic compound of claim 1, wherein $Ar_1$ comprises a group represented by one of Formulae 7-1 to 7-12:

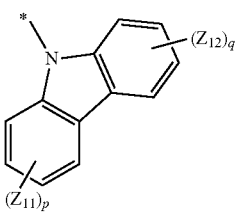

7-1

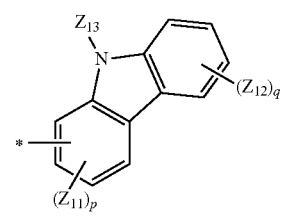

7-2

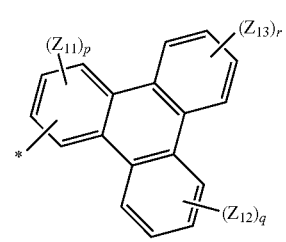

7-3

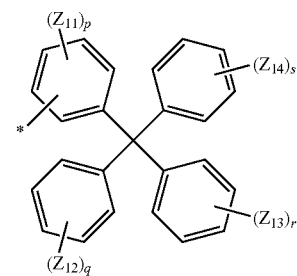

7-4

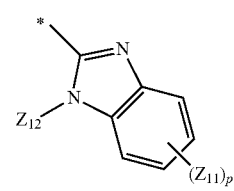

7-5

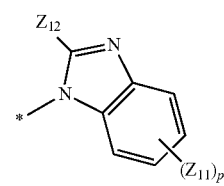

7-6

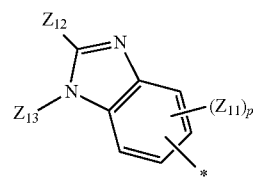

7-7

-continued

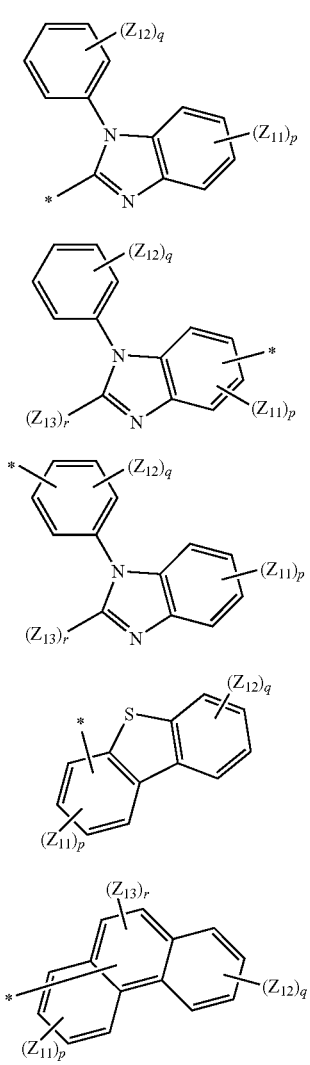

wherein:

each of $Z_{11}$ to $Z_{14}$ independently comprises at least one of:
- a hydrogen atom;
- a heavy hydrogen atom;
- a halogen atom;
- a hydroxyl group;
- a cyano group;
- a nitro group;
- an amino group;
- an amidino group;
- hydrazine;
- hydrazone;
- a carboxyl group or a salt thereof;
- a sulfonic acid group or a salt thereof;
- a phosphoric acid group or a salt thereof;
- a $C_1$-$C_{10}$ alkyl group;
- a $C_1$-$C_{10}$ alkoxy group;
- a $C_1$-$C_{10}$ alkyl group or a $C_1$-$C_{10}$ alkoxy group substituted with at least one selected from the group consisting of a heavy hydrogen atom, a halogen atom, a hydroxyl group, a cyano group, a nitro group, an amino group, an amidino group, hydrazine, hydrazone, a carboxyl group or a salt thereof, a sulfonic acid group or a salt thereof, and a phosphoric acid group or a salt thereof;
- a phenyl group;
- a naphthyl group;
- a fluorenyl group;
- a phenanthrenyl group;
- an anthryl group;
- a pyrenyl group;
- a chrysenyl group;
- a phenyl group, a naphthyl group, a fluorenyl group, a phenanthrenyl group, an anthryl group, a pyrenyl group, or a chrysenyl group substituted with at least one selected from the group consisting of a heavy hydrogen atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{10}$ alkyl group, and a $C_1$-$C_{10}$ alkoxy group;
- an indolyl group;
- a benzoimidazolyl group;
- a carbazolyl group;
- an imidazolyl group;
- an imidazolinyl group;
- an imidazopyridinyl group;
- an imidazopyrimidinyl group;
- a pyridinyl group;
- a pyrimidinyl group;
- a triazinyl group;
- a quinolinyl group; or
- an indolyl group, a benzoimidazolyl group, a carbazolyl group, an imidazolyl group, an imidazolinyl group, an imidazopyridinyl group, a pyridinyl group, a pyrimidinyl group, a triazinyl group, or a quinolinyl group substituted with at least one selected from the group consisting of a heavy hydrogen atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, and a naphthyl group; and each of p, q, r and s is independently an integer from 1 to 5.

9. The heterocyclic compound of claim 1, wherein $Ar_1$ comprises a group represented by one of Formulae 8-1 to 8-20:

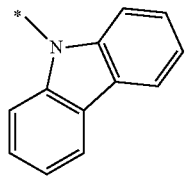

8-1

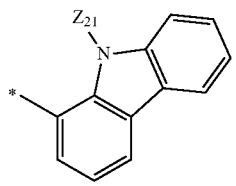

8-2

-continued
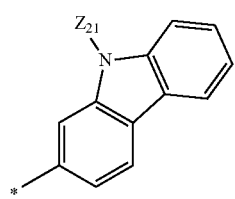
8-3
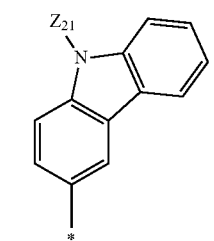
8-4
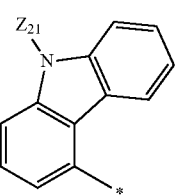
8-5
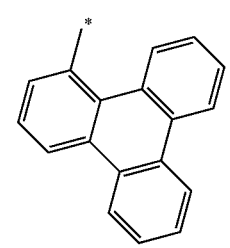
8-6
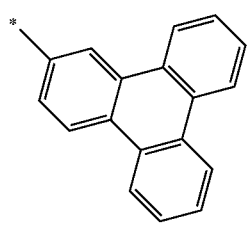
8-7
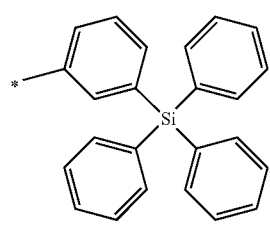
8-8
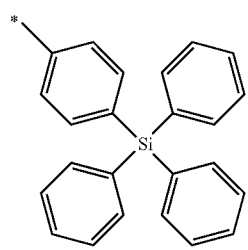
8-9
-continued
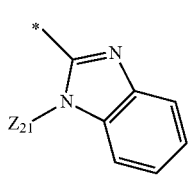
8-10
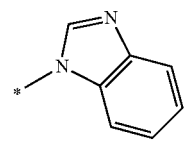
8-11
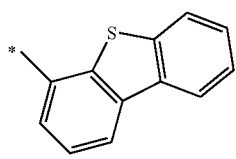
8-12
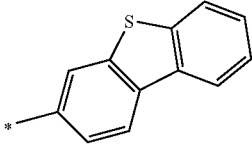
8-13
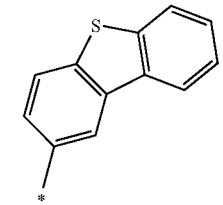
8-14
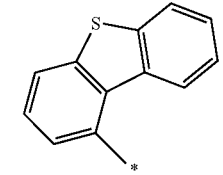
8-15
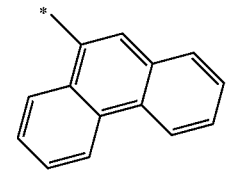
8-16
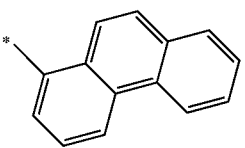
8-17
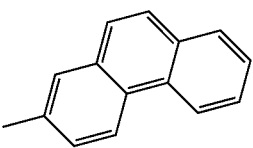
8-18

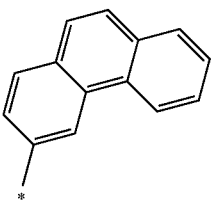

8-19

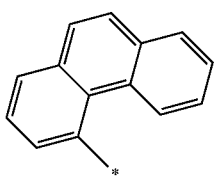

8-20 wherein $Z_{21}$ comprises a hydrogen atom, a heavy hydrogen atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a fluorenyl group, a phenanthrenyl group, an anthryl group, a pyrenyl group, a chrysenyl group, an indolyl group, a benzoimidazolyl group, a carbazolyl group, an imidazolyl group, an imidazolinyl group, an imidazopyridinyl group, an imidazopyrimidinyl group, a pyridinyl group, a pyrimidinyl group, a triazinyl group, or a quinolinyl group.

10. The heterocyclic compound of claim 1, wherein $L_1$ comprises a substituted or unsubstituted phenylene group, a substituted or unsubstituted pentalenylene group, a substituted or unsubstituted indenylene group, a substituted or unsubstituted naphthylene group, a substituted or unsubstituted azulenylene group, a substituted or unsubstituted heptalenylene group, a substituted or unsubstituted indacenylene group, a substituted or unsubstituted acenaphthylene group, a substituted or unsubstituted fluorenylene group, a substituted or unsubstituted phenalenylene group, a substituted or unsubstituted phenanthrenylene group, a substituted or unsubstituted anthrylene group, a substituted or unsubstituted fluoranthenylene group, a substituted or unsubstituted triphenylenylene group, a substituted or unsubstituted pyrenylene group, a substituted or unsubstituted chrysenylene group, a substituted or unsubstituted naphthacenylene group, a substituted or unsubstituted picenylene group, a substituted or unsubstituted perylenylene group, a substituted or unsubstituted pentaphenylene group, a substituted or unsubstituted hexacenylene group, a substituted or unsubstituted pyrrolylene group, a substituted or unsubstituted pyrazolylene group, a substituted or unsubstituted imidazolylene group, a substituted or unsubstituted imidazolinylene group, a substituted or unsubstituted imidazopyridinylene group, a substituted or unsubstituted imidazopyrimidinylene group, a substituted or unsubstituted pyridinylene group, a substituted or unsubstituted pyrazinylene group, a substituted or unsubstituted pyrimidinylene group, a substituted or unsubstituted indolylene group, a substituted or unsubstituted purinylene group, a substituted or unsubstituted quinolinylene group, a substituted or unsubstituted phthalazinylene group, a substituted or unsubstituted indolizinylene group, a substituted or unsubstituted naphthyridinylene group, a substituted or unsubstituted quinazolinylene group, a substituted or unsubstituted cinnolinylene group, a substituted or unsubstituted indazolylene group, a substituted or unsubstituted carbazolylene group, a substituted or unsubstituted phenazinylene group, a substituted or unsubstituted phenanthridinylene group, a substituted or unsubstituted pyranylene group, a substituted or unsubstituted chromenylene group, a substituted or unsubstituted furanylene group, a substituted or unsubstituted benzofuranylene group, a substituted or unsubstituted thiophenylene group, a substituted or unsubstituted benzothiophenylene group, a substituted or unsubstituted isothiazolylene group, a substituted or unsubstituted benzoimidazolylene group, a substituted or unsubstituted isoxazolylene group, a substituted or unsubstituted dibenzothiophenylene group, a substituted or unsubstituted dibenzopuranylene group, a substituted or unsubstituted triazinylene group, or a substituted or unsubstituted oxadiazolylene.

11. The heterocyclic compound of claim 1, wherein $L_1$ comprises a group represented by one of Formulae 9-1 to 9-17:

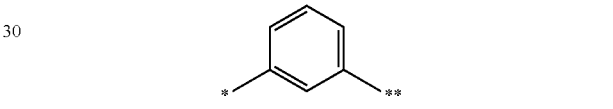

9-1

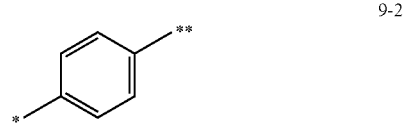

9-2

9-3

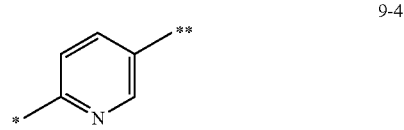

9-4

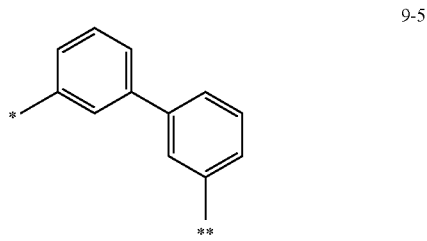

9-5

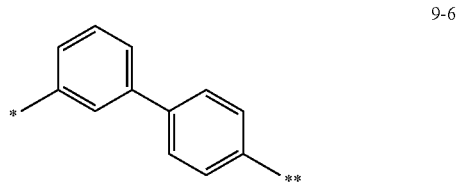

9-6

57
-continued
9-7
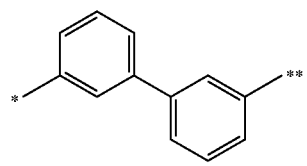
9-8
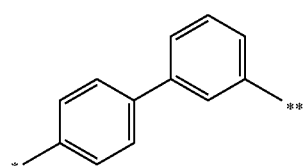
9-9
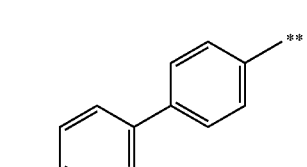
9-10
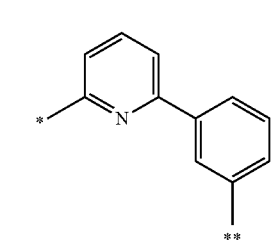
9-11
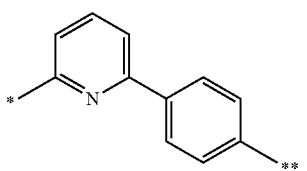
9-12
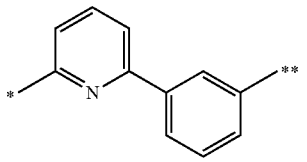
9-13
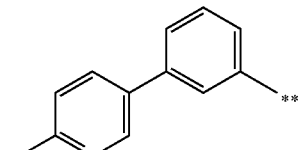
9-14
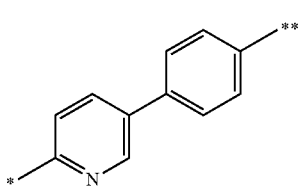
58
-continued
9-15
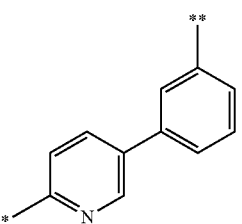
9-16
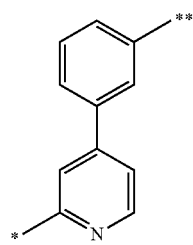
9-17
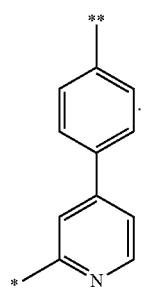
12. The heterocyclic compound of claim 1, wherein the compound represented by Formula 1 comprises one of Compounds 1 to 48:
1
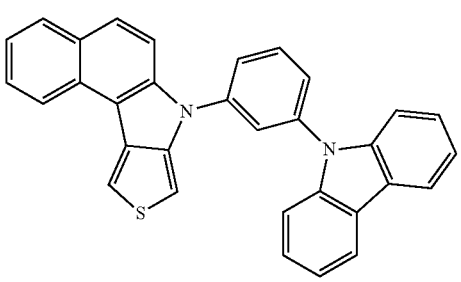
2
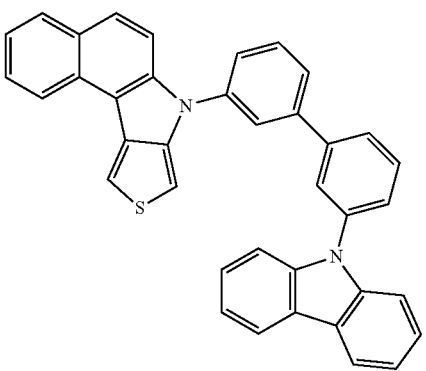

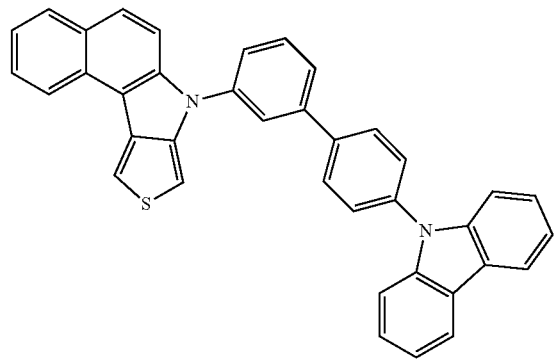
3
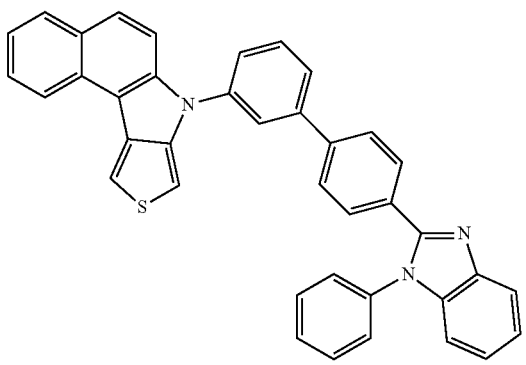
7
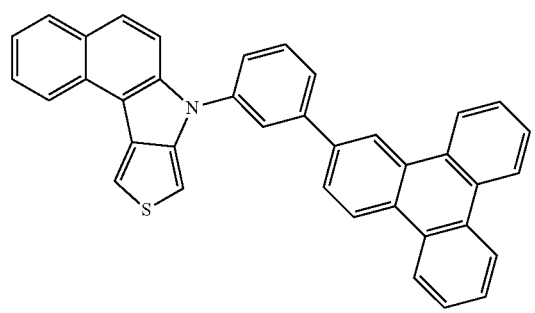
4
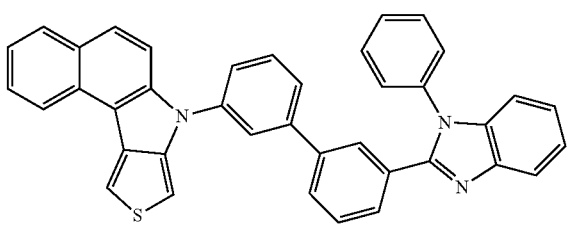
8
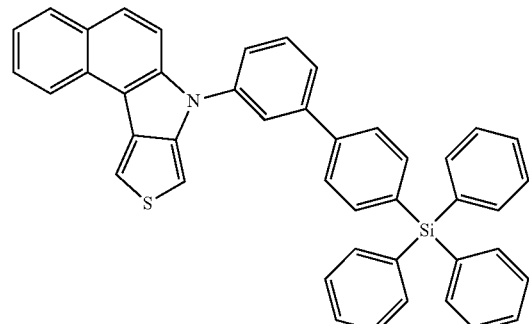
5
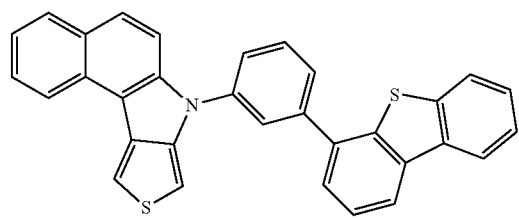
9
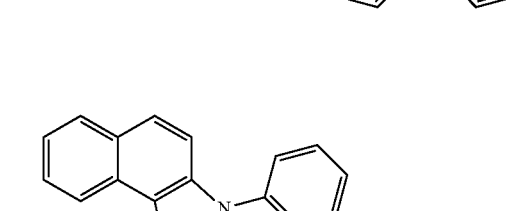
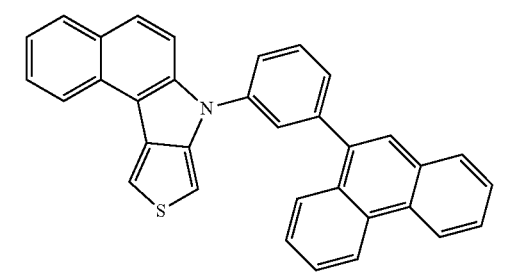
10
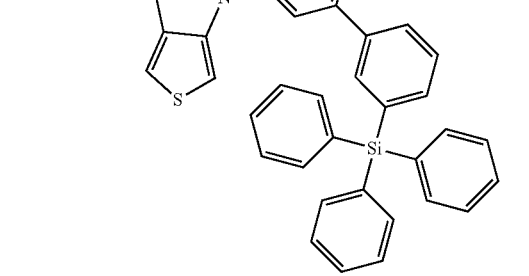
6
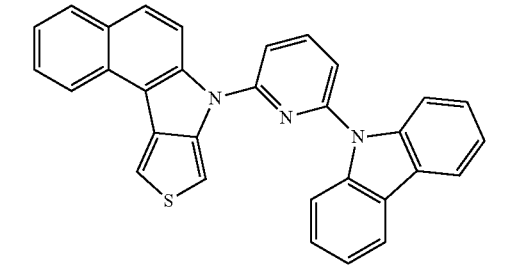
11

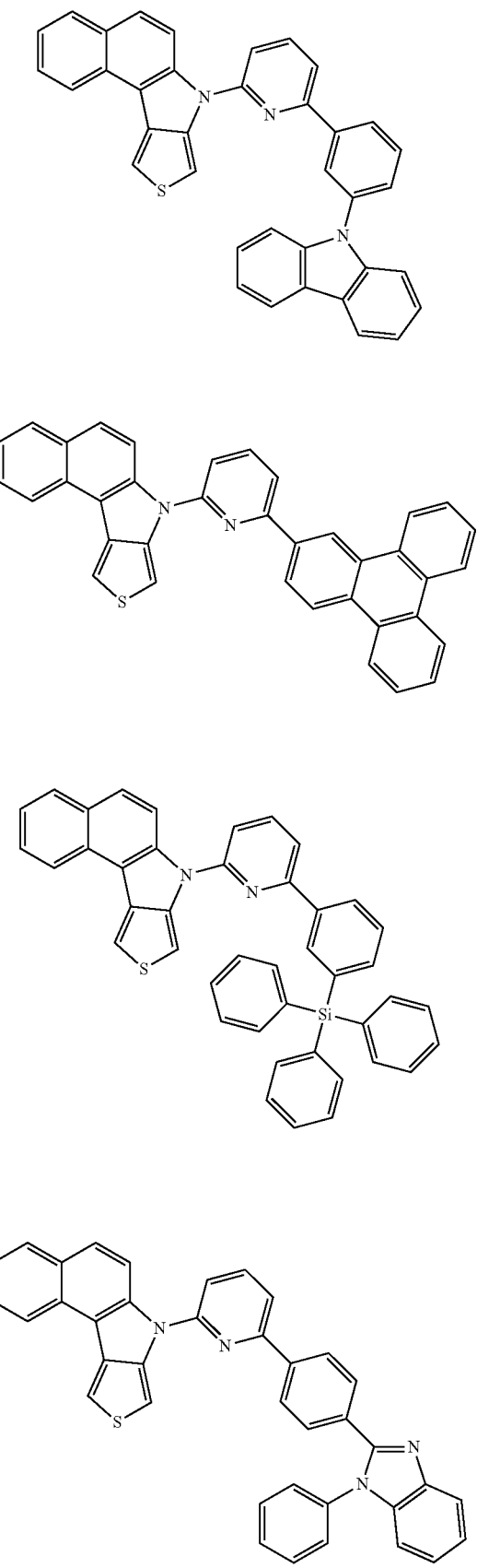
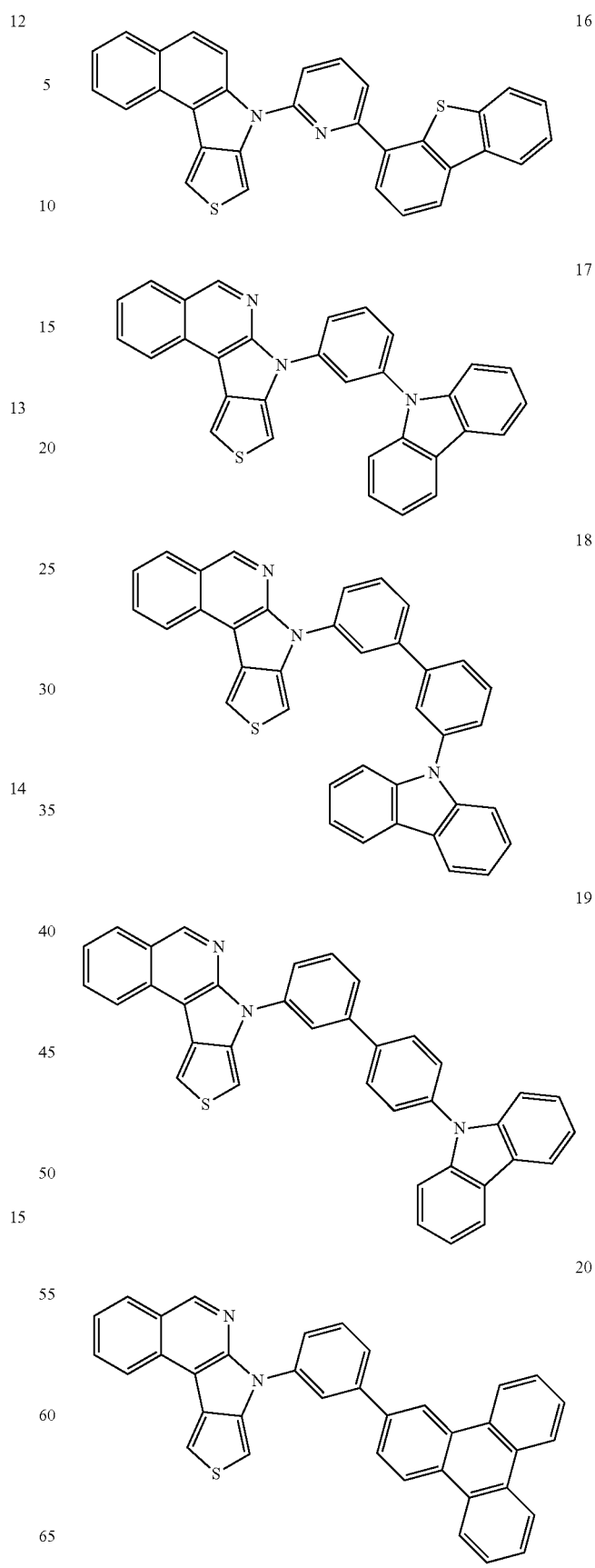

21
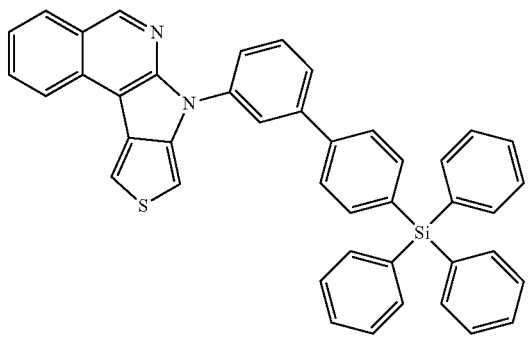
22
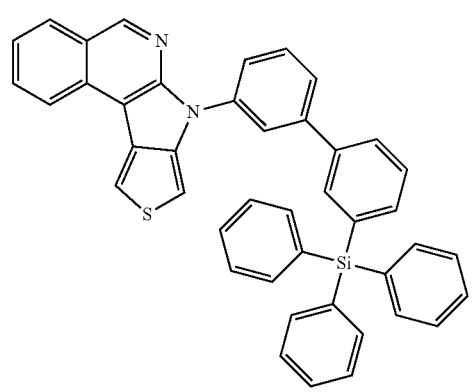
23
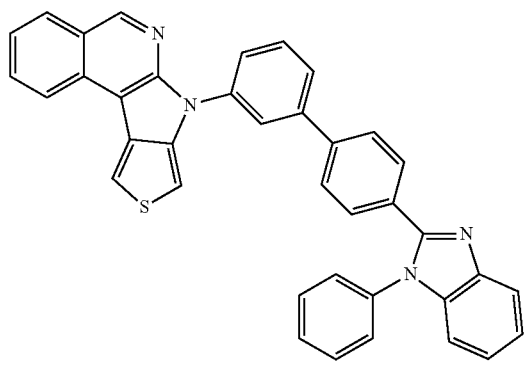
24
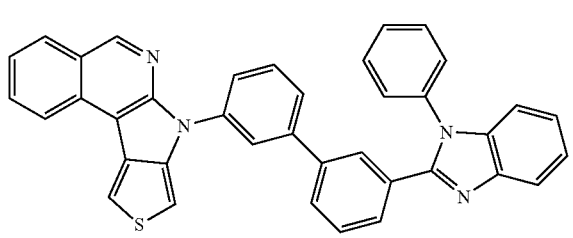
25
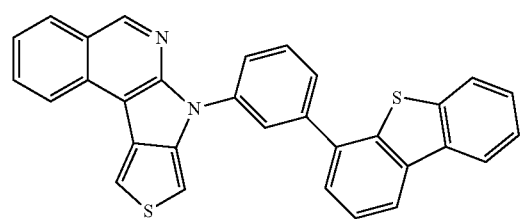
26
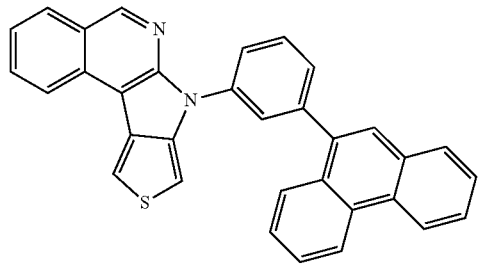
27
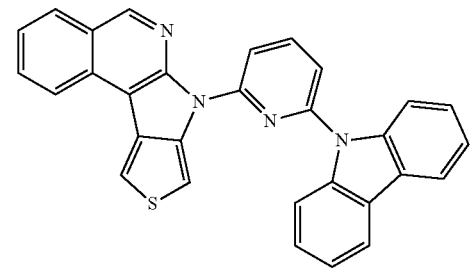
28
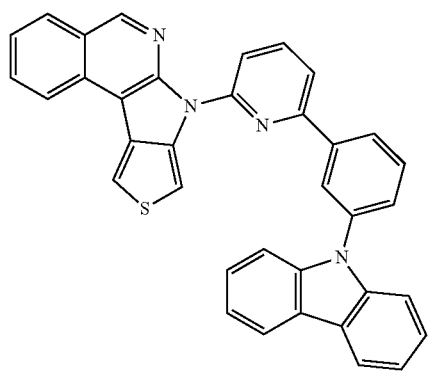
29
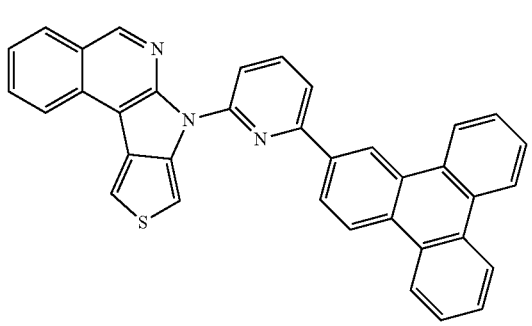
30
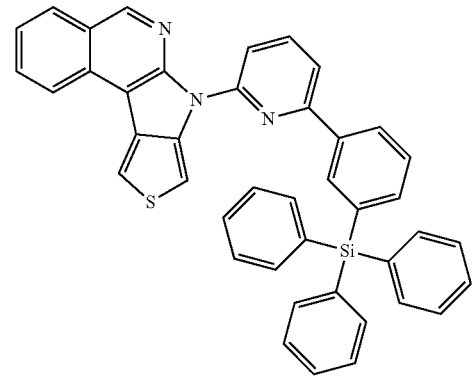

31
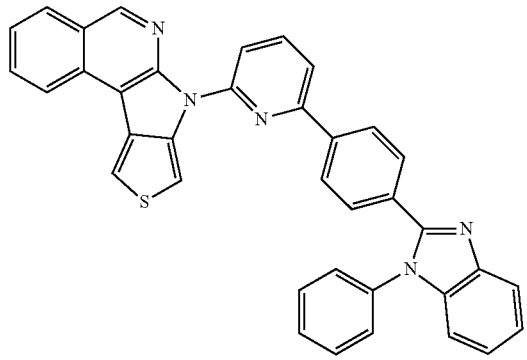
32
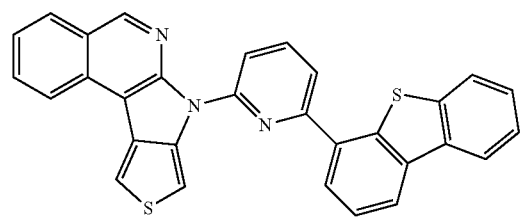
33
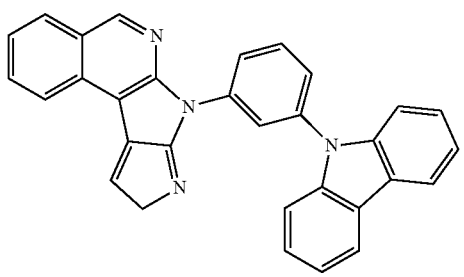
34
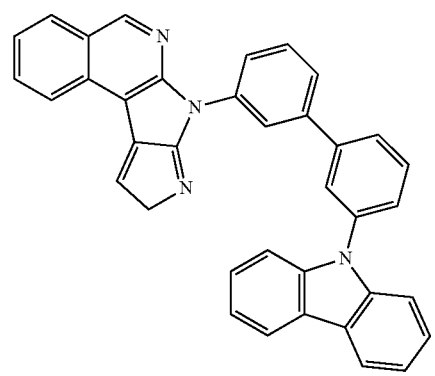
35
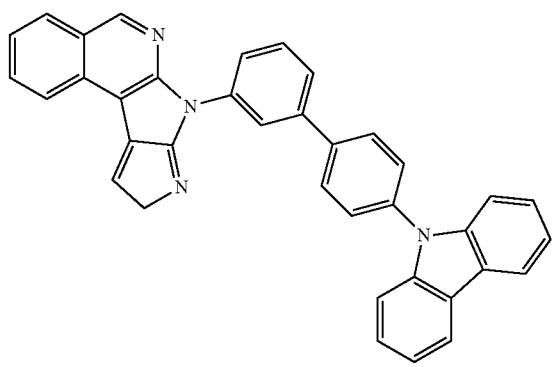
36
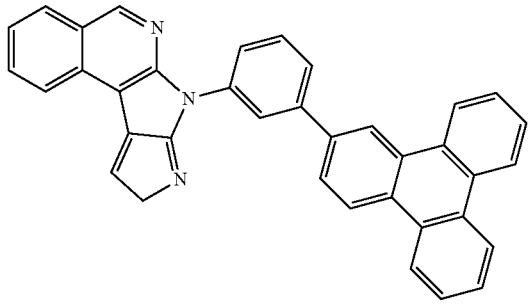
37
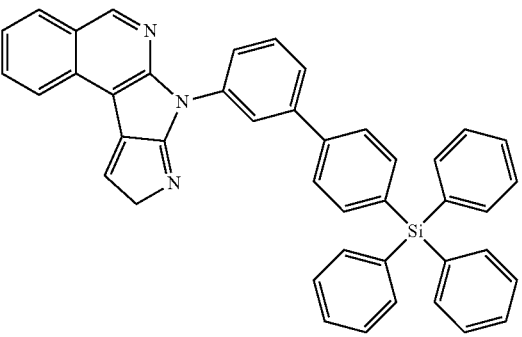
38
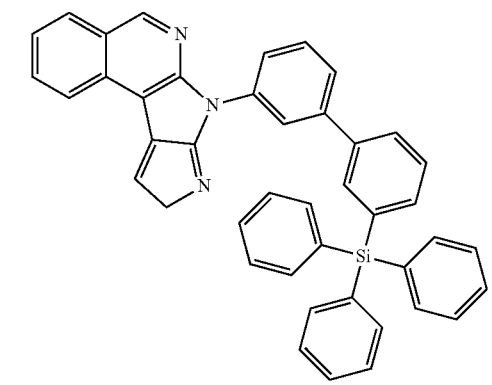
39
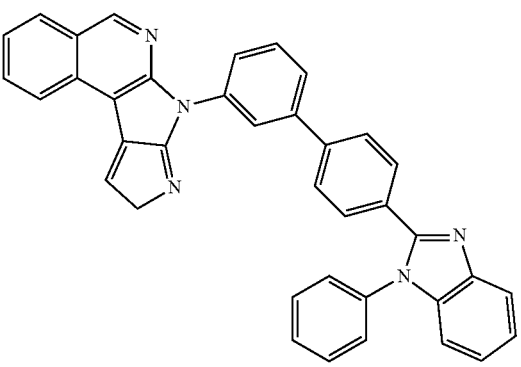

67

-continued

40

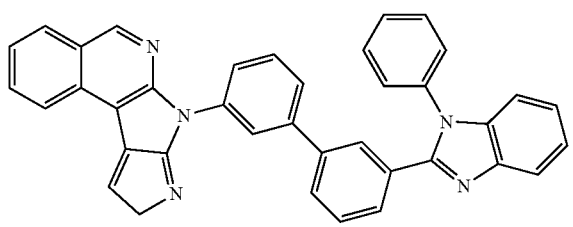

41

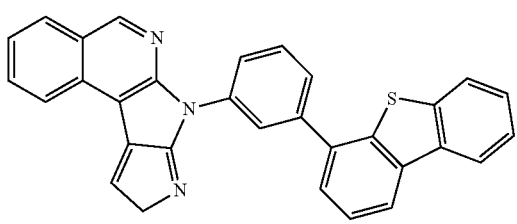

42

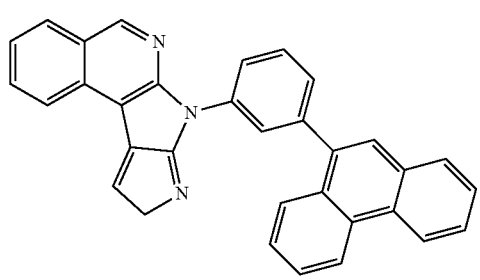

43

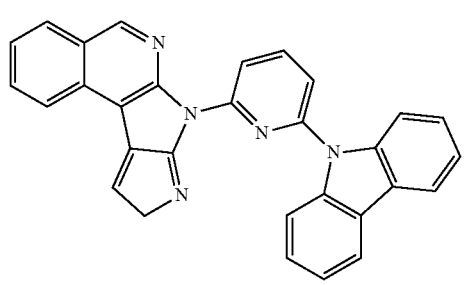

44

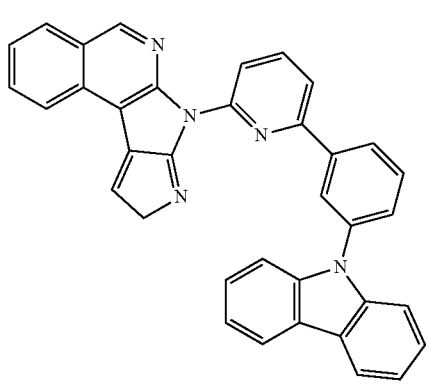

68

-continued

45

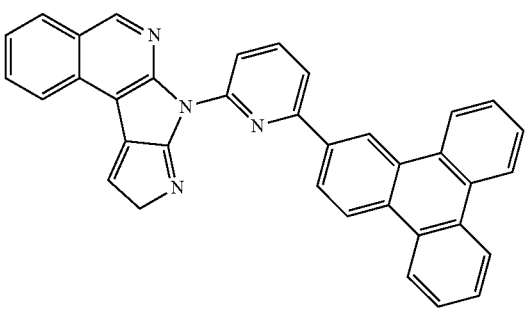

46

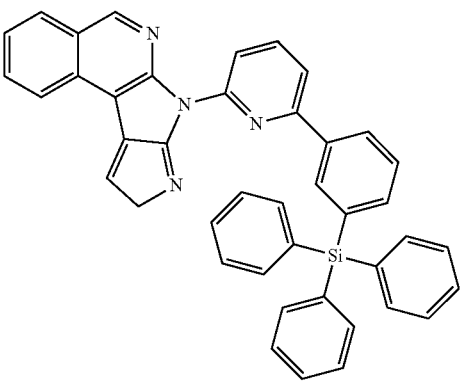

47

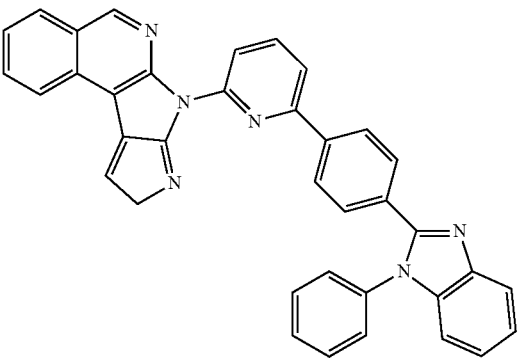

48

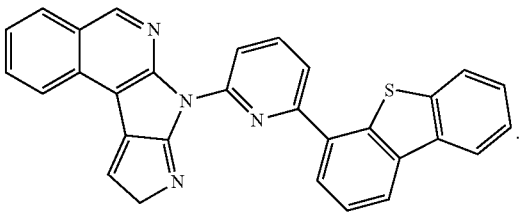

13. An organic light-emitting diode comprising: a first electrode; a second electrode disposed opposite to the first electrode; and an organic layer between the first electrode and the second electrode, wherein the organic layer comprises the heterocyclic compound according to claim 1.

14. The organic light-emitting diode of claim 13, wherein the organic layer comprises at least one of a hole injection layer, a hole transport layer, or a functional layer having both hole injecting and hole transporting capabilities, and at least one of the hole injection layer, the hole transport layer, or the functional layer having both hole injecting and hole transporting capabilities comprises the heterocyclic compound.

15. The organic light-emitting diode of claim 13, wherein the organic layer comprises at least one of an electron injection layer, an electron transport layer, or a functional layer having both electron injecting and electron transporting capabilities, and at least one of the electron injection layer, the electron transport layer, or the functional layer having both electron injecting and electron transporting capabilities comprises the heterocyclic compound.

16. The organic light-emitting diode of claim 13, wherein the organic layer comprises an emission layer comprising the heterocyclic compound.

17. The organic light-emitting diode of claim 16, wherein the heterocyclic compound contained in the emission layer functions as a phosphorescent host.

18. The organic light-emitting diode of claim 13, wherein the organic layer comprises an emission layer, and at least one of an electron injection layer, an electron transport layer, or a functional layer having both electron injecting and electron transporting capabilities, wherein the emission layer comprises an arylamine compound.

19. The organic light-emitting diode of claim 13, wherein the organic layer comprises an electron transport layer that comprises an electron transporting material and a metal complex.

20. A flat panel display device, comprising the organic light-emitting device of claim 13 and a transistor, the transistor comprising a source, a drain, a gate, and an active layer,
   wherein the first electrode of the organic light-emitting diode is electrically connected to the source or the drain of the transistor.

* * * * *